United States Patent
Szott

(10) Patent No.: US 11,748,817 B2
(45) Date of Patent: Sep. 5, 2023

(54) SYSTEMS AND METHODS FOR GENERATING AN ASSESSMENT OF SAFETY PARAMETERS USING SENSORS AND SENSOR DATA

(71) Applicant: Allstate Insurance Company, Northbrook, IL (US)

(72) Inventor: Debra Szott, Palatine, IL (US)

(73) Assignee: ALLSTATE INSURANCE COMPANY, Northbrook, IL (US)

(*) Notice: Subject to any disclaimer, the term of this patent is extended or adjusted under 35 U.S.C. 154(b) by 0 days.

(21) Appl. No.: 16/364,238

(22) Filed: Mar. 26, 2019

(65) Prior Publication Data
US 2019/0304025 A1 Oct. 3, 2019

Related U.S. Application Data

(60) Provisional application No. 62/648,691, filed on Mar. 27, 2018.

(51) Int. Cl.
*G06Q 40/08* (2012.01)
*G01N 33/00* (2006.01)
*G01W 1/00* (2006.01)

(52) U.S. Cl.
CPC ......... *G06Q 40/08* (2013.01); *G01N 33/0075* (2013.01); *G01W 1/00* (2013.01)

(58) Field of Classification Search
CPC ...... G06Q 40/08; G01N 33/0075; G01W 1/00
See application file for complete search history.

(56) References Cited

U.S. PATENT DOCUMENTS

| | | |
|---|---|---|
| 6,006,333 A | 12/1999 | Nielsen |
| D426,206 S | 6/2000 | Richter |

(Continued)

FOREIGN PATENT DOCUMENTS

| | | |
|---|---|---|
| CN | 101252627 A | 8/2008 |
| CN | 107239967 A | 10/2017 |
| EP | 1320004 A1 | 6/2003 |

OTHER PUBLICATIONS

Evelyn L. Kent, "Cognitive computing The human benefit of natural language processing" dated May 31, 2016, KMWorld https://www.kmworld.com/Articles/News/News-Analysis/Cognitive-computing--The-human-benefit-of-natural-language-processing-111268.aspx#:\ (Year: 2016).*

(Continued)

*Primary Examiner* — Gregory S Cunningham, II
*Assistant Examiner* — Raven E Yono
(74) *Attorney, Agent, or Firm* — Dinsmore & Shohl LLP

(57) ABSTRACT

Systems and methods are disclosed for generating an assessment of safety parameters using sensors and sensor data. One method may include, receiving, by a computing device having one or more processors and from a user device, a request for generating an neighborhood safety assessment for a desired geographic area, wherein the request is based on an assessment of a first neighborhood safety parameter of a plurality of neighborhood safety parameters; determining, by the computing device, one or more sensors associated with the desired geographic area; receiving, by the computing device in real time and from the one or more sensors, a present value for a characteristic of the first neighborhood safety parameter of the one or more neighborhood safety parameters; and generating, based on the received present value, an assessment of the first neighborhood safety param- (Continued)

eter of the one or more neighborhood safety parameters for the desired geographic area.

17 Claims, 5 Drawing Sheets

(56) References Cited

U.S. PATENT DOCUMENTS

| | | |
|---|---|---|
| D434,419 S | 11/2000 | Bomze et al. |
| 6,233,563 B1 | 5/2001 | Jefferson et al. |
| 6,298,229 B1 | 10/2001 | Tomlinson, Jr. et al. |
| D453,767 S | 2/2002 | Istvan et al. |
| 6,415,226 B1 | 7/2002 | Kozak |
| 6,430,542 B1 | 8/2002 | Moran |
| D464,660 S | 10/2002 | Weng et al. |
| 6,493,629 B1 | 12/2002 | Van Bosch |
| 6,522,265 B1 | 2/2003 | Hillman et al. |
| D474,479 S | 5/2003 | Tambata |
| D474,780 S | 5/2003 | Tambata |
| D475,719 S | 6/2003 | Horie |
| 6,677,854 B2 | 1/2004 | Dix |
| 6,726,107 B1 | 4/2004 | Ruth |
| 6,745,153 B2 | 6/2004 | White et al. |
| D495,338 S | 8/2004 | Peter et al. |
| 6,771,742 B2 | 8/2004 | McCalmont et al. |
| 6,847,825 B1 | 1/2005 | Duvall et al. |
| D517,087 S | 3/2006 | Sands |
| 7,012,993 B2 | 3/2006 | Alton |
| 7,024,205 B1 | 4/2006 | Hose |
| 7,027,808 B2 | 4/2006 | Wesby |
| D522,015 S | 5/2006 | Cummins et al. |
| D523,442 S | 6/2006 | Hiramatsu |
| 7,068,994 B2 | 6/2006 | Van Camp |
| 7,091,903 B2 | 8/2006 | Kim |
| 7,092,695 B1 | 8/2006 | Boling et al. |
| 7,099,835 B2 | 8/2006 | Williams, III |
| D529,507 S | 10/2006 | Cummins |
| D529,510 S | 10/2006 | Cummins et al. |
| 7,119,669 B2 | 10/2006 | Lundsgaard et al. |
| 7,130,406 B2 | 10/2006 | Pines et al. |
| 7,142,959 B2 | 11/2006 | Oesterling et al. |
| 7,155,335 B2 | 12/2006 | Rennels |
| 7,167,796 B2 | 1/2007 | Taylor et al. |
| 7,174,243 B1 | 2/2007 | Lightner et al. |
| 7,215,965 B2 | 5/2007 | Fournier et al. |
| D544,871 S | 6/2007 | Lim et al. |
| 7,236,576 B2 | 6/2007 | Schnarel et al. |
| 7,242,966 B1 | 7/2007 | Averkamp |
| D550,689 S | 9/2007 | Vigesaa |
| 7,266,435 B2 | 9/2007 | Wang et al. |
| D553,146 S | 10/2007 | Byeon et al. |
| 7,289,786 B2 | 10/2007 | Krasner |
| D556,770 S | 12/2007 | O'Donnell et al. |
| D560,226 S | 1/2008 | Jung et al. |
| 7,323,973 B1 | 1/2008 | Ceglia et al. |
| D561,191 S | 2/2008 | Haning et al. |
| 7,336,172 B2 | 2/2008 | Govindaraj |
| D563,975 S | 3/2008 | Vigesaa |
| D564,541 S | 3/2008 | Lettau et al. |
| 7,343,565 B2 | 3/2008 | Ying et al. |
| D565,581 S | 4/2008 | Gunn et al. |
| 7,389,244 B2 | 6/2008 | Kaplan |
| 7,405,537 B2 | 7/2008 | Hoffman et al. |
| D574,842 S | 8/2008 | Kwag et al. |
| D575,302 S | 8/2008 | Millar et al. |
| 7,421,321 B2 | 9/2008 | Breed et al. |
| D578,134 S | 10/2008 | Jasinski |
| D579,946 S | 11/2008 | Lee et al. |
| 7,457,693 B2 | 11/2008 | Olsen et al. |
| 7,460,019 B2 | 12/2008 | Henderson |
| 7,463,951 B2 | 12/2008 | Ampunan et al. |
| 7,480,546 B2 | 1/2009 | Kamdar et al. |
| D586,355 S | 2/2009 | Mori et al. |
| 7,487,111 B2 | 2/2009 | Shoen et al. |
| 7,499,714 B2 | 3/2009 | Ki |
| D592,223 S | 5/2009 | Neuhaus |
| D593,110 S | 5/2009 | Danton |
| D593,111 S | 5/2009 | Danton |
| D594,465 S | 6/2009 | Hong et al. |
| D594,468 S | 6/2009 | Bamford et al. |
| 7,593,855 B1 | 9/2009 | Craig |
| 7,602,388 B2 | 10/2009 | Plut |
| D605,657 S | 12/2009 | Danton |
| D607,464 S | 1/2010 | Tang et al. |
| D608,366 S | 1/2010 | Matas |
| D611,056 S | 3/2010 | Langlois et al. |
| D618,249 S | 6/2010 | Ahn et al. |
| D618,696 S | 6/2010 | Woods et al. |
| D618,700 S | 6/2010 | Song |
| D618,702 S | 6/2010 | Lee |
| D621,849 S | 8/2010 | Anzures et al. |
| 7,777,648 B2 | 8/2010 | Smith et al. |
| D623,555 S | 9/2010 | Reithlingshoefer et al. |
| D624,556 S | 9/2010 | Chaudhri |
| D624,589 S | 9/2010 | Robbins |
| 7,802,722 B1 | 9/2010 | Papierniak et al. |
| D625,312 S | 10/2010 | Jewitt et al. |
| 7,813,980 B2 | 10/2010 | Crockett |
| D631,889 S | 2/2011 | Vance et al. |
| D642,194 S | 7/2011 | Kozlowski et al. |
| D645,051 S | 9/2011 | Kozlowski et al. |
| 8,140,358 B1 | 3/2012 | Ling et al. |
| 8,166,026 B1 | 4/2012 | Sadler |
| 8,285,571 B2 | 10/2012 | Demirdjian et al. |
| 8,289,171 B2 | 10/2012 | Morley |
| 8,315,792 B2 | 11/2012 | Speier et al. |
| 8,375,032 B2 | 2/2013 | Birdwell et al. |
| 8,606,512 B1 | 12/2013 | Bogovich et al. |
| 8,645,014 B1 | 2/2014 | Kozlowski et al. |
| 8,738,422 B2 | 5/2014 | Lerner et al. |
| 8,750,902 B2 | 6/2014 | Xiao et al. |
| 8,781,657 B2 | 7/2014 | Pebbles |
| 8,799,034 B1 | 8/2014 | Brandmaier et al. |
| 8,805,603 B1 | 8/2014 | Cavallaro Kozlowski et al. |
| 8,805,707 B2 | 8/2014 | Schumann, Jr. et al. |
| 8,959,156 B2 | 2/2015 | Polis et al. |
| 9,297,723 B1 | 3/2016 | Hofmann et al. |
| 9,384,491 B1 | 7/2016 | Briggs et al. |
| 9,406,228 B1 | 8/2016 | Kozlowski et al. |
| 9,411,982 B1 | 8/2016 | Dippenaar et al. |
| 9,412,130 B2 | 8/2016 | Wasserman et al. |
| 9,497,585 B1 * | 11/2016 | Cooley ................ H04W 4/029 |
| 9,659,301 B1 | 5/2017 | Briggs et al. |
| 9,674,156 B2 | 6/2017 | Stiglic et al. |
| 9,684,924 B2 | 6/2017 | Wasserman et al. |
| 9,692,815 B2 | 6/2017 | Caldwell |
| 9,697,525 B1 | 7/2017 | Kozlowski et al. |
| 9,881,268 B1 | 1/2018 | Briggs et al. |
| 10,186,134 B1 * | 1/2019 | Moon ................ G08B 25/006 |
| 2002/0055861 A1 | 5/2002 | King et al. |
| 2002/0065703 A1 | 5/2002 | Garg |
| 2002/0073012 A1 | 6/2002 | Lowell et al. |
| 2002/0096561 A1 | 7/2002 | Sullivan |
| 2002/0184653 A1 | 12/2002 | Pierce et al. |
| 2003/0088347 A1 | 5/2003 | Ames |
| 2004/0024711 A1 | 2/2004 | Camping et al. |
| 2004/0100363 A1 | 5/2004 | Lane et al. |
| 2004/0100479 A1 | 5/2004 | Nakano et al. |
| 2004/0111195 A1 | 6/2004 | Vries et al. |
| 2004/0192336 A1 | 9/2004 | Walby |
| 2004/0203850 A1 | 10/2004 | Oesterling |
| 2004/0221239 A1 | 11/2004 | Hachigian et al. |
| 2005/0027438 A1 | 2/2005 | Rockett et al. |
| 2005/0071052 A1 | 3/2005 | Coletrane et al. |
| 2005/0091272 A1 | 4/2005 | Smith et al. |
| 2005/0144114 A1 | 6/2005 | Ruggieri et al. |
| 2005/0187833 A1 | 8/2005 | Royer et al. |
| 2005/0197771 A1 | 9/2005 | Seick et al. |
| 2005/0261986 A1 | 11/2005 | Haynes et al. |
| 2006/0022846 A1 | 2/2006 | Tummala |
| 2006/0123360 A1 | 6/2006 | Anwar et al. |
| 2006/0245570 A1 | 11/2006 | Pfleging et al. |
| 2006/0247852 A1 | 11/2006 | Kortge et al. |
| 2006/0291633 A1 | 12/2006 | Glaza et al. |

(56) References Cited

U.S. PATENT DOCUMENTS

| | | |
|---|---|---|
| 2007/0011278 A1 | 1/2007 | Nou |
| 2007/0033540 A1 | 2/2007 | Bridges et al. |
| 2007/0043770 A1* | 2/2007 | Goodrich ............ G06F 3/04817 |
| 2007/0066276 A1 | 3/2007 | Kuz et al. |
| 2007/0072625 A1 | 3/2007 | Fournier et al. |
| 2007/0088473 A1 | 4/2007 | Moon et al. |
| 2007/0122026 A1 | 5/2007 | Ersue et al. |
| 2007/0135990 A1 | 6/2007 | Seymour et al. |
| 2007/0139182 A1 | 6/2007 | O'Connor et al. |
| 2007/0142026 A1 | 6/2007 | Kuz et al. |
| 2007/0167147 A1 | 7/2007 | Krasner et al. |
| 2007/0185728 A1 | 8/2007 | Schwarz et al. |
| 2007/0226783 A1 | 9/2007 | Mimlitsch |
| 2007/0240079 A1 | 10/2007 | Flynt et al. |
| 2007/0244628 A1 | 10/2007 | Rockett et al. |
| 2007/0252689 A1 | 11/2007 | Rothschild |
| 2007/0298765 A1 | 12/2007 | Dickinson et al. |
| 2008/0004790 A1 | 1/2008 | Ames |
| 2008/0014908 A1 | 1/2008 | Vasant |
| 2008/0054072 A1 | 3/2008 | Katragadda et al. |
| 2008/0119203 A1 | 5/2008 | Shalmon et al. |
| 2008/0140287 A1 | 6/2008 | Yang et al. |
| 2008/0167937 A1 | 7/2008 | Coughlin et al. |
| 2008/0177653 A1 | 7/2008 | Famolari et al. |
| 2008/0215240 A1 | 9/2008 | Howard et al. |
| 2008/0261554 A1 | 10/2008 | Keller et al. |
| 2008/0306982 A1 | 12/2008 | Moudy |
| 2008/0319665 A1 | 12/2008 | Berkobin et al. |
| 2009/0002145 A1 | 1/2009 | Berry et al. |
| 2009/0072995 A1 | 3/2009 | Thomas et al. |
| 2009/0088967 A1* | 4/2009 | Lerner .................. G01C 21/32 701/532 |
| 2009/0093236 A1 | 4/2009 | Balan et al. |
| 2009/0125178 A1 | 5/2009 | Wilson |
| 2009/0210142 A1 | 8/2009 | Couckuyt et al. |
| 2009/0216600 A1 | 8/2009 | Hill |
| 2009/0233572 A1 | 9/2009 | Basir |
| 2009/0287527 A1 | 11/2009 | Kolb et al. |
| 2010/0070487 A1 | 3/2010 | Fetsch |
| 2010/0138242 A1 | 6/2010 | Ferrick et al. |
| 2010/0161382 A1 | 6/2010 | Cole |
| 2010/0207787 A1 | 8/2010 | Catten et al. |
| 2010/0332133 A1 | 12/2010 | Harris et al. |
| 2011/0082816 A1 | 4/2011 | Moffett |
| 2011/0213628 A1* | 9/2011 | Peak ...................... G06Q 40/08 705/4 |
| 2011/0238999 A1 | 9/2011 | Lee et al. |
| 2012/0136743 A1 | 5/2012 | McQuade et al. |
| 2012/0179363 A1 | 7/2012 | Pierfelice |
| 2013/0183924 A1* | 7/2013 | Saigh ...................... A61K 9/08 455/404.2 |
| 2014/0222618 A1 | 8/2014 | Stamp et al. |
| 2014/0358943 A1* | 12/2014 | Raymond .............. G06Q 10/10 707/748 |
| 2015/0012303 A1* | 1/2015 | Ghosh .................... G06Q 50/16 705/306 |
| 2015/0026088 A1* | 1/2015 | Alber .................... G06Q 50/265 705/325 |
| 2015/0161867 A1* | 6/2015 | Bell ........................ G08B 21/22 340/539.13 |
| 2015/0207786 A1 | 7/2015 | Pitroda |
| 2015/0242814 A1 | 8/2015 | Saad |
| 2015/0326548 A1 | 11/2015 | Marson et al. |
| 2016/0048934 A1 | 2/2016 | Gross |
| 2016/0086082 A1* | 3/2016 | Babinowich ........... G06Q 50/16 706/46 |
| 2016/0140299 A1 | 5/2016 | Al Harbi |
| 2016/0155201 A9 | 6/2016 | Bell |
| 2016/0232598 A1 | 8/2016 | Wasserman et al. |
| 2016/0337394 A1 | 11/2016 | Crowley et al. |
| 2017/0011465 A1* | 1/2017 | Anastassov ............ G06Q 40/08 |
| 2017/0249702 A1 | 8/2017 | Wasserman et al. |
| 2017/0301048 A1 | 10/2017 | Turek et al. |
| 2018/0053110 A1* | 2/2018 | Kang ........................ G06N 7/01 |
| 2018/0073879 A1* | 3/2018 | Hakeem .................. B64C 39/02 |
| 2018/0189147 A1* | 7/2018 | Banasik .............. G06F 11/2069 |
| 2018/0189913 A1* | 7/2018 | Knopp .................. H04W 4/021 |
| 2018/0218446 A1 | 8/2018 | Ries et al. |
| 2019/0156655 A1* | 5/2019 | Cordes .................... H04W 4/90 |

OTHER PUBLICATIONS

Definition Cognitive Computing by TechTarget, dated Jul. 2018 https://searchenterpriseai.techtarget.com/definition/cognitive-computing#:~: (Year: 2018).*

"Deep Learning 3 things you need to know," MathWorks, dated Jul. 18, 2017 https://www.mathworks.com/discovery/deep-learning.html (Year: 2017).*

Jun. 14, 2019—(WO) International Search Report & Written Opinion—PCT/US 19/024272.

Allstate Motor Club Launches Roadside Assistance Mobile App for iPhone and BlackBerry Users, Oct. 27, 2009; http://money.cnn.com/news/newsfeeds/articles/prnewswire/2009102711, 2 pages.

TMC News, ATX Launches Enhanced Automatic Collision Notification for BMW, Jan. 11, 2009, http://tmcnet.com/usubmit/2009/01/11/3905139.htm, 4 pages.

Automotive Fleet, Aug. 2009, vol. 48, No. 9, Charging for Preventable Accidents: What's the Payoff?, Grace Lauron, 4 pages.

Automotive Fleet, May 2009, Bright Ideas Energize Fleet Management, Cindy Brauer and Thi Dao, 5 pages.

Automotive Fleet, Sep. 2009 Vol. 48 No. 10, DWT Proven to Increase Accidents, Grace Lauron, 5 pages.

Motorola DemonsliaLes New Communications System Available in BMW's Global 2005 Model Year Vehicle Line, http://www.virtualizationconference.com/49572/print, 2 pages, retrieved on Feb. 6, 2009.

BMW Assist, Safety & Convenience Services © 2006 BMW of North America, LLC, 16 pages.

Automotive Fleet, Emkay Partners With Networkcar to Launch New Networkfleet Telematics Solution, Apr. 29, 2008, © 2009 Automotive Fleet, 1 page.

Geotab Management by Measurement, Geotab for Insurance Companies © 2008, 1 page.

CIO, High-tech Cars: The Coolest Automotive Technologies, Denise Dubie, Network World, Oct. 5, 2008, http://www.cio.com/article/print/452913, retrieved on Feb. 6, 2009, 2 pages.

Inrix News, INRIX Real-Time Traffic Now Available on Over 75 Navigation and Mobile Devices, Jul. 30, 2007, http://www.inrix.com/news_75Devices_30July2007.asp, retrieved Feb. 6, 2009, 1 page.

ABIresearch, Wireless Connectivity to the Automobile Is Hindered by Lack of Standards and Interoperability, Jul. 31, 2007, http://www.abiresearch.com/abiprdisplay.jsp?pressid=894, retrieved on Feb. 6, 2009, 1 page.

When Accidents Happen, Nationwide Mobile App for IPhone is on Your Side, Melanie Broemsen, May 10, 2009, http://www articlesbase.com/print/909297, retrieved on Jun. 23, 2009, 1 page.

Diagnostic Trouble Codes (DTCs) Powertrain Codes for OBD II (OBD-2) equipped GM vehicles, compiled by Anthony W. Haukap; http://myweb.accessus.net/~090/dtocbd2p.html; retrieved on Jul. 20, 2009, 20 pages.

Automotive Fleet, OnStar Receives Honors at Telematics Update Awards © 2009 Automotive Fleet, http://www.automotive-fleet.com/News/Print/Story/2008/05/OnStar Receives, retrieved on Feb. 6, 2009, 1 page.

Real time traffic broadcast to debut in Australia, http://www.gpsbusinessnews.com, retrieved Feb. 6, 2009 1 page.

ABIresearch, In-Vehicle Infotainment Storage and Networking, Hard Disks, Flash Memory, USB, SD, Bluetooth, UWB, iPod Kits and Other Technologies, http://www.abiresearch.com/producs/market_research/In-Vehicle_Infotainment, retrieved on Feb. 6, 2009, 2 pages.

Techworld, Pimp your ride: Cool car technology, Denise Dubie (Network World) Jul. 10, 2008; http://www.techworld.com/au/article/262977/pimp_your_ride_cool_car, retrieved on Feb. 6, 2009, 3 pages.

(56) References Cited

OTHER PUBLICATIONS

Maya Software Technologies, White Paper, Automotive Telematics—Market Overview and Security Considerations © 2001, 12 pages.
Intomobile, Volkswagen Launches iPhone Optimized Website Featuring Access to Emergency Roadside Assistance, http://www.intomobile.com/2009/03/30/volkswagen-launches-iPhone-optimized-website-featuring-access, retrieved on Jun. 23, 2009, 3 pages.
RepairPal for iPhone, http://repairpal.com/mobile, retrieved Feb. 2, 2009, 13 pages.
Tradevibes, The RepairPal iPhone App is Available! © 2007-2008 Mill River Labs, www.tradevibes.com/news/view/repairpal?article=86228, retrieved on Feb. 2, 2009, 1 page.
Übergizm™, RepairPal: Roadside Assistance from the iPhone, posted Jan. 22, 2009, http://www.ubergizmo.com/15/archives/2009/01/repairpal_roadside_assistance, retrieved on Feb. 2, 2009, 1 page.
Automotive Fleet, Sep. 2009 Vol. 48 No. 10, 10 Recommendations: What Drivers Should Do After a Fleet Accident, Mike Antich, 4 pages.
Automotive Fleet/2009 NAFA Planning Guide, NAFA 2009 Institute & Expo Advanced Planning Guide, 2 pages.
U.S. Appl. No. 29/396,366, filed Jun. 29, 2011.
U.S. Copyright Registration No. TX 7-150-082, "Mini Road Assist", registered on Mar. 19, 2010.
U.S. Copyright Registration No. TX 7-329-434, "Mini Road Assist", registered on Mar. 19, 2010.
U.S. Copyright Registration No. TX 7-150-080, "Mini Road Assist", registered Mar. 29, 2010.
U.S. Copyright Registration No. TX 7-195-526, "Allstate Motor Club Roadside Assistance", registered Mar. 30, 2010.
U.S. Copyright Registration No. TX 7-229-997, "Allstate Motor Club Roadside Assistance", registered Mar. 19, 2010.
U.S. Copyright Registration No. TX 7-150-076, "Allstate Motor Club Roadside Assistance", registered Mar. 26, 2010.
Jan. 16, 2013—U.S. Non-Final Office Action—U.S. Appl. No. 12/859,634.
Jun. 7, 2013—U.S. Notice of Allowance—U.S. Appl. No. 12/859,634.
Jul. 25, 2012—U.S. Non-Final Office Action—U.S. Appl. No. 12/859,627.
Jan. 15, 2013—U.S. Final Office Action—U.S. Appl. No. 12/859,627.
"Roadside Assistance with Emergency Roadside Service", http://www.geico.com/getaquote/auto/emergency-road-service/, downloaded Feb. 25, 2015, pp. 1-5.
BoatUS Towing App—Free for All Boaters—BoatUS, http://www.boatus.com/towing/app.asp, downloaded Feb. 25, 2015, pp. 1-2.
Software Engineering for Service-Oriented Overlay Computers, D1.4a: UML for Service-Oriented Systems, Sensoria, Oct. 10, 2007, pp. 1-21.
Lapadula, A., COWS Specification of the On Road Assistance Scenario, Dec. 19, 2007, pp. 1-9.
Mar. 23, 2015—U.S. Non Final Office Action—U.S. Appl. No. 13/446,192.
Mar. 23, 2015—U.S. Non Final Office Action—U.S. Appl. No. 13/446,146.
Mar. 13, 2015—U.S. Notice of Allowance—U.S. Appl. No. 12/859,627.
May 26, 2015—U.S. Non-Final Office Action—U.S. Appl. No. 13/446,146.
Feb. 17, 2016—U.S. Notice of Allowance—U.S. Appl. No. 13/446,192.
Mar. 17, 2016—(WO) International Search Report and Written Opinion—App PCT/US16/14044.
May 4, 2016—U.S. Notice of Allowance—U.S. Appl. No. 14/444,247.
Jun. 27, 2016—U.S. Notice of Allowance—U.S. Appl. No. 14/721,689.
Aug. 23, 2016—U.S. Non-Final Office Action—U.S. Appl. No. 13/446,146; KFS does not cite OAs as prior art.
Sep. 9, 2016—U.S. Non-Final Office Action—U.S. Appl. No. 14/989,390.
Sep. 15, 2016—U.S. Non-Final Office Action—U.S. Appl. No. 14/959,402.
Oct. 31, 2016—U.S. Notice of Allowance—U.S. Appl. No. 15/058,371.
Oct. 7, 2016—U.S. Office Action—U.S. Appl. No. 15/135,101.
Dec. 16, 2016—U.S. Non-Final Office—U.S. Appl. No. 14/959,438.
Jan. 20, 2017—U.S. Notice of Allowance—U.S. Appl. No. 14/959,402.
Feb. 17, 2017—U.S. Notice of Allowance—U.S. Appl. No. 13/446,146.
Mar. 3, 2017—U.S. Final Office Action—U.S. Appl. No. 14/989,390.
Mar. 10, 2017—U.S. Notice of Allowance—U.S. Appl. No. 15/135,101.
Nov. 20, 2015—U.S. Non-Final Office Action—U.S. Appl. No. 14/611,915.
Dec. 9, 2013—U.S. Non-Final Office Action—U.S. Appl. No. 13/961,000.
Apr. 6, 2016—U.S. Final Office Action—U.S. Appl. No. 13/446,146.
Apr. 4, 2017—U.S. Notice of Allowance—U.S. Appl. No. 14/959,438.
Sep. 20, 2017—U.S. Notice of Allowance—U.S. Appl. No. 14/989,390.
Nov. 2, 2017—U.S. Non-Final Office Action—U.S. Appl. No. 15/180,416.
Nov. 2, 2017—U.S. Non-Final Office Action—U.S. Appl. No. 15/258,312.
Nov. 16, 2017—U.S. Non-Final Office Action—U.S. Appl. No. 15/593,529.
Mar. 27, 2018—U.S. Notice of Allowance—U.S. Appl. No. 15/593,529.
May 18, 2018 U.S. Non-Final Office Action—U.S. Appl. No. 15/180,416.
May 31, 2018—U.S. Non-Final Office Action—U.S. Appl. No. 15/463,594.
May 31, 2018—U.S. Non-Final Office Action—U.S. Appl. No. 15/598,732.
Jun. 15, 2018—U.S. Notice of Allowance—U.S. Appl. No. 15/258,312.
Jun. 4, 2018—(CA) Office Action—App 2,975,450.
Jun. 25, 2018—U.S. Non-Final Office Action—U.S. Appl. No. 15/482,954.
Jun. 22, 2018—(EP) Supplementary European Search Report—EP16746952.
Anonymous: "On-Board Diagnostics—Wikipedia", Jan. 29, 2015, XP055478209.
Sep. 6, 2018—U.S. Non-Final Office Action—U.S. Appl. No. 15/398,256.
Nov. 13, 2018—U.S. Non-Final Office Action—U.S. Appl. No. 15/819,066.
Jan. 31, 2019—U.S. Final Office Action—U.S. Appl. No. 15/482,954.
The Sweet Setup, How to use 1Password as a digital will, https://thesweetsetup.com/1password-digital-will, Aug. 15, 2018, 8 pages.
Mylennium, Digital Asset Toolbox, https://www.mylennium.com/digital-asset-toolbox, Jan. 21, 2019, 4 pages.
Deseat.me, Clean up your online presence, https://www.deseat.me, Jan. 21, 2019, 5 pages.
Kiplinger, Protect Digital Assets After Your Death, https://www.kiplinger.com/article/retirement/T021-C000-S004-protect-digital-assets-after-your-death.html, Jan. 21, 2019, 5 pages.
AfterVault, The Digital Beyond, http://www.thedigitalbeyond.com/online-services-list/aftervault, Jan. 21, 2019, 3 pages.
Yodlee, Account Aggregation Software: What it Is and Howto Choose It, https://www.yodlee.com/trending/content/account-aggregation-software-what-it-and-how-choose-it, Jan. 21, 2019, 8 pages.
Ernie Feirer "Strategic Visualization: Evolving How You View Commercial Property Insurance Underwriting" LexisNexis website: https://www.lexisnexis.com/risk/downloads/assets/strategic-visualization-wp.pdf Sep. 2015, pp. 1-6.
"Underwriting and Rating Integrity" Verisk Analytics, Inc. website: https://www.verisk.com/insurance/capabilities/underwriting/property/underwriting-and-rating-integrity/ visited Dec. 20, 2018, pp. 1-7.
Xinrong Li "Catastrophe Model Suitability Analysis: Quantitative Scoring" Cass Business School City University London website: https://www.scor.com/fr/files/actuarial-award-2014-uk-catastrophe-model-suitability-analysis-quantitative-scoring Aug. 2013, pp. 1-71.
"Expand your real estate investment horizons" Location Inc website: https://locationinc.com/industry-solutions/real-estate-data/ website visited Dec. 21, 2018, pp. 1-7.
Jennifer Nicole Dowling "Finding Your Best-Fit Neighborhood: A Web GIS Application for Online Residential Property Searches for Anchorage, Alaska" Thesis Presented to the Faculty of the USC Graduate School website: https://spatial.usc.edu/wp-content/uploads/2014/10/DowlingJennifer.pdf Dec. 2014, pp. 1-41.
Mar. 15, 2019—U.S. Notice of Allowance—U.S. Appl. No. 15/398,256.

(56) References Cited

OTHER PUBLICATIONS

Jul. 23, 2019—(WO) International Search Report and Written Opinion—PCT/US19/24202.
May 8, 2020—U.S. Non-Final Office Action—U.S. Appl. No. 16/365,290.

* cited by examiner

SYSTEMS AND METHODS FOR GENERATING AN ASSESSMENT OF SAFETY PARAMETERS USING SENSORS AND SENSOR DATA

RELATED APPLICATIONS

This application claims priority to U.S. provisional application No. 62/648,691, filed on Mar. 27, 2018, and which is hereby incorporated by reference herein.

TECHNICAL FIELD

Aspects of the disclosure generally relate to sensors and computer hardware and software. In particular, various aspects of the disclosure include a framework for generating an assessment of neighborhood safety parameters using sensors and sensor data.

BACKGROUND

When an individual is looking to move to an area he or she is not familiar with, he or she may not be aware of problems that may be typically associated with the area, such as the crime rate, an increased risk of flood or fire, or the like. An individual moving to a new area may be interested in information that is current (e.g., in real time), reliable, and from a trusted source. Without accurate information associated with a particular area, insurance providers might not be able to accurately assess neighborhood risk and the impact of such risk, and real estate prices may not accurately reflect the effects of neighborhood safety. There is also a desire for this information to be accessible to users on a user interface having intuitive functionalities. The present disclosure may address one or more of the shortcomings described above.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of the disclosure relate to systems, methods, apparatuses and computer-readable media for generating parameters for neighborhood safety using sensors and sensor data.

One example method may include: receiving, by a computing device having one or more processors and from a user device, a request for generating a neighborhood safety assessment for a desired geographic area. The request may be based on an assessment of a first neighborhood safety parameter of a plurality of neighborhood safety parameters. The computing device may determine or identify one or more sensors associated with the desired geographic area; and receive, from the one or more sensors, a present value for a characteristic of the first neighborhood safety parameter of the one or more neighborhood safety parameters. The present value may be received by the computing device or measured by the sensors in real time. The computing device may generate, based on the received present value, an assessment of the first neighborhood safety parameter of the one or more neighborhood safety parameters for the desired geographic area. Assessments of other neighborhood safety parameters of the one or more neighborhood safety parameters may also be generated.

The method may further comprise: receiving, by the computing device and via an electronic storage medium, a past value for the characteristic of the first neighborhood safety parameter; and comparing the received past value to the received present value of the characteristic of the first neighborhood safety parameter. The comparison may be used to generate a catastrophe model for the desired geographic area. The assessment of the first neighborhood safety parameter for the desired geographic area may be further based on the comparison of the received past value to the received present value and/or on the catastrophe model.

Neighborhood safety parameters may include, for example, environmental parameters and social parameters. A characteristic of an environmental parameter may include, for example, a pollutant level, a pollen level, a precipitation level, a temperature; an indication of humidity, a wind speed or velocity, an indication of a weather event or upcoming weather event; a seismograph reading, a characteristic of a terrain, or an indication of a microbe or disease presence.

A characteristic of a social parameter may include, for example, a frequency of, a severity of, or a count of a crime or misdemeanor; a frequency, severity, or a count of a civil unrest; a frequency, severity, or a count of a cybercrime; or a count of residents or workers in the desired geographical area with a criminal record.

In accordance with other embodiments of the present disclosure, another example method comprises: receiving, by a computing device having one or more processors and from a user device, a request for generating an neighborhood safety assessment for a desired geographic area, wherein the request is based on an assessment of a first neighborhood safety parameter of a plurality of neighborhood safety parameters; receiving, by the computing device, an electronic file at least one insurance claim associated with the first neighborhood safety parameter for the desired geographic area; recognizing, using the one or more processors of the computing device and from the electronic copy of at least one insurance claim, one or more terms associated with the first neighborhood safety parameter; and generating, based on the recognized one or more terms, a value of a characteristic of the first neighborhood safety parameter; generating an assessment of the first neighborhood safety parameter for the desired geographic area based on the value of the characteristic of the first neighborhood safety parameter.

In accordance with other embodiments of the present disclosure, an example system comprises: one or more processors; and memory storing computer-executable instructions that, when executed by the one or more processors, cause the system to: receive, from a user device, a request for generating an neighborhood safety assessment for a desired geographic area, wherein the request is based on an assessment of a first neighborhood safety parameter of a plurality of neighborhood safety parameters; identify one or more sensors associated with the desired geographic area; receive, in real time and from the one or more sensors, a present value for a characteristic of the first neighborhood safety parameter of the one or more neighborhood safety parameters; and generate, based on the received present value, an assessment of the first neighborhood safety parameter of the one or more neighborhood safety parameters for the desired geographic area.

Other features and advantages of the disclosure will be apparent from the additional description provided herein.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein.

DETAILED DESCRIPTION

In the following description of the various embodiments, reference is made to the accompanying drawings, which form a part hereof, and in which is shown by way of illustration, various embodiments of the disclosure that may be practiced. It is to be understood that other embodiments may be utilized.

As will be appreciated by one of skill in the art upon reading the following disclosure, various aspects described herein may be embodied as a method, a computer system, or a computer program product. Accordingly, those aspects may take the form of an entirely hardware embodiment, an entirely software embodiment or an embodiment combining software and hardware aspects. Furthermore, such aspects may take the form of a computer program product stored by one or more computer-readable storage media having computer-readable program code, or instructions, embodied in or on the storage media. Any suitable computer readable storage media may be utilized, including hard disks, CD-ROMs, optical storage devices, magnetic storage devices, and/or any combination thereof. In addition, various signals representing data or events as described herein may be transferred between a source and a destination in the form of electromagnetic waves traveling through signal-conducting media such as metal wires, optical fibers, and/or wireless transmission media (e.g., air and/or space).

At a high level, systems and methods are disclosed for creating a model and/or safety score(s) using various applicable data (e.g., claims data, catastrophe models (CATs), weather data, crime data, etc.). The models and/or scores could be made available to consumers, through real estate or other property or neighborhood focused websites, who may be interested in purchasing the scores and/or models or through an entity's quote process where it could result in recommendations for additional policies or coverages. When an individual is looking to move to an area he or she is not familiar with, he or she may not be aware of problems that may be typically associated with the area, such as the crime rate, an increased risk of flood or fire, or the like. For example, a prospective buyer may not realize that an area has an increased flood or fire risk. An individual could use the models and/or scores as a way to become more familiar and comfortable with a neighborhood, for example, when moving to or seeking to establish oneself in a new area. Furthermore, the scoring could lead to increased coverage limits, more products bought or changes to the property to reduce risk.

Figure 1:
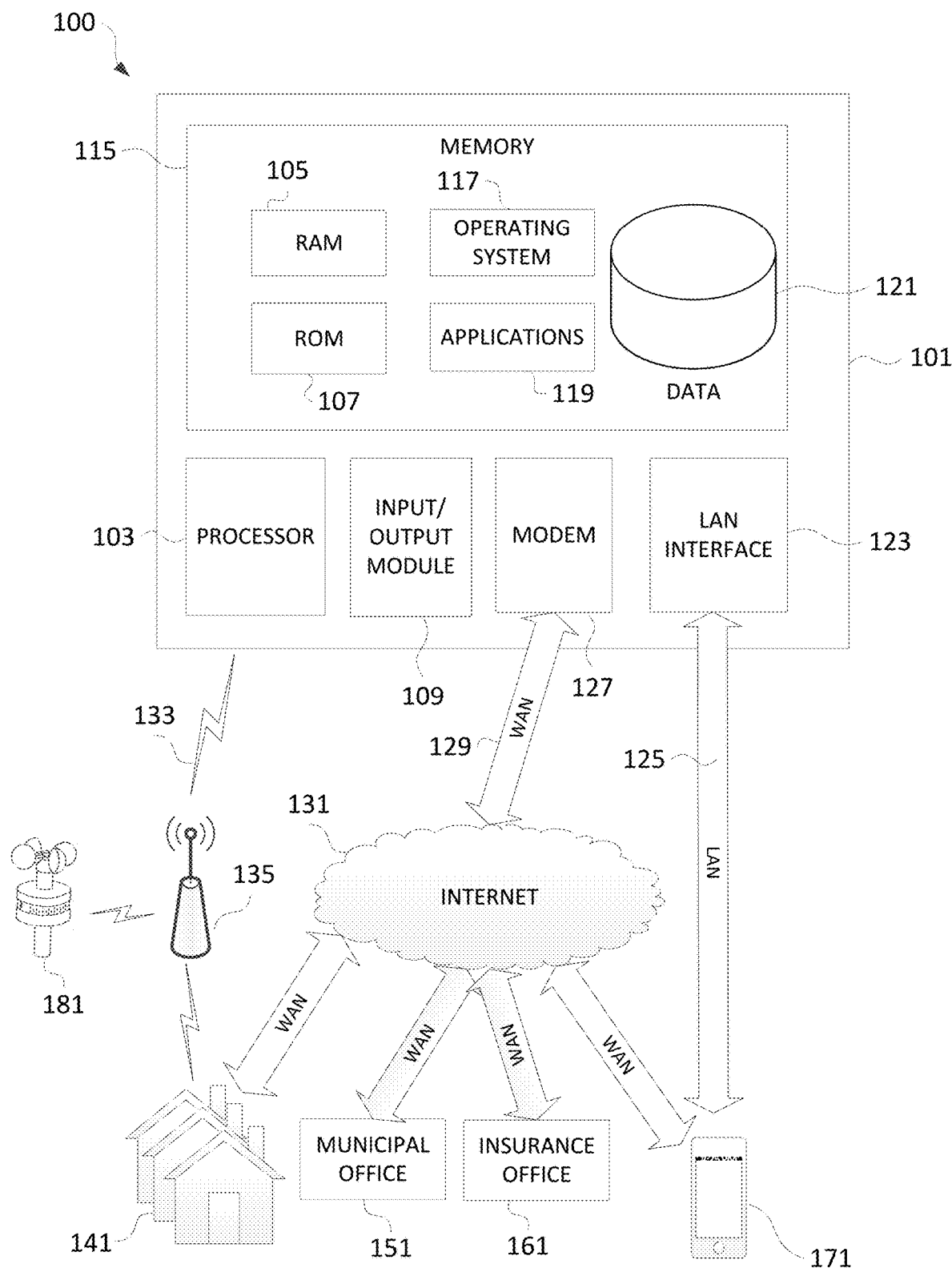
FIG. 1 illustrates a network environment and computing systems that may be used to implement aspects of the disclosure.

FIG. 1 illustrates a block diagram of a computing device (or system) 101 in communication system 100 that may be used according to one or more illustrative arrangements of the disclosure. The device 101 may have a processor 103 for controlling overall operation of the device 101 and its associated components, including input/output device 109, and memory 115. The computing device 101, along with one or more environmental sensors 181 (e.g., weather and/or geological sensors), one or more computing systems (e.g., terminals 141, 151, 161, and 171) may correspond to any of multiple systems or devices, such as various servers or systems. For example, these systems may include, for example, computing system or systems for use inside or outside homes or neighborhoods (e.g., terminal 141); computing system or systems at municipal offices 151 for collecting and/or processing municipal information (e.g., crime reports, fire records, property damage records, suspicious activity, etc.); computing system or systems at insurance offices or agencies 161 for receiving, verifying, and/or processing insurance claims that may pertain to issues affecting neighborhood safety; and user device or devices 171 for accessing, analyzing, researching, and/or generating neighborhood safety parameters.

Input/Output (I/O) 109 may include a microphone, keypad, touch screen, and/or stylus through which a user of the computing device 101 may provide input, and may also include one or more of a speaker for providing audio output and a video display device for providing textual, audiovisual and/or graphical output. Software may be stored within memory 115 and/or storage to provide instructions to processor 103 for enabling device 101 to perform various functions. For example, memory 115 may store software used by the device 101, such as an operating system 117, application programs 119, and an associated internal database 121. Further memory 115 may include random access memory (RAM) 105 and read-only memory (ROM) 107. Processor 103 and its associated components may allow the system 101 to execute a series of computer-readable instructions, e.g., to receive requests for generating neighborhood safety parameters for a desired area, establish connections with and send queries to external computing systems, process natural language input, generate a characteristic or value for a neighborhood safety parameter, determine a quantifiable effect of a neighborhood safety parameter on a property value, and/or determine a quantifiable effect of a neighborhood safety parameter on an insurance condition.

The system 101 may operate in a networked environment 100 supporting connections to one or more remote computers, such as terminals 141, 151, 161, and 171. The terminals 141, 151, 161, and 171 may be personal computers, servers (e.g., web servers, database servers), or mobile communication devices (e.g., mobile phones, portable computing devices, and the like), and may include some or all of the elements described above with respect to the sensing or monitoring system 101. The network connections depicted in FIG. 1 include a local area network (LAN) 125 and a wide area network (WAN) 129, and a wireless telecommunications network 133, but may also include other networks. When used in a LAN networking environment, the system 101 may be connected to the LAN 125 through a network interface or adapter 123. When used in a WAN networking environment, the system 101 may include a modem 127 or other means for establishing communications over the WAN 129, such as network 131 (e.g., the Internet). When used in a wireless telecommunications network 133, the system 101 may include one or more transceivers, digital signal processors, and additional circuitry and software for communicating with wireless computing devices 141 (e.g., mobile phones, portable computing devices, and the like) via one or more network devices 135 (e.g., base transceiver stations) in the wireless network 133.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, WiFi, WiMAX, and wireless mesh networks, is presumed, and the various computing devices and system components described herein may be configured to communicate using any of these network protocols or technologies.

Additionally, one or more application programs 119 used by the system 101 may include computer-executable instructions for receiving data of a present or past characteristic for one or more of a plurality of neighborhood safety parameters, and generating a safety assessment of a desired area based on the received data. The data may be received from environmental sensors 181 (e.g., weather stations, seismographs and other geological sensors, pollutant sensors, satellite cameras or sensors, drone cameras or sensors, etc.) Furthermore, one or more application programs 119 used by the sensing system 101 may include computer-readable instructions for comparing the past characteristic to the present characteristic for the one or more neighborhood safety parameters and generating a catastrophe or disaster model for the desired area, e.g., based on the comparison. The application programs 119 may also be used to communicate any sensed or determined data to other users for alerting them to neighborhood safety conditions so that they can take preventive action. The application program 119 may also be used to assist in generating a total assessment of a neighborhood's safety based on assessments of one or more neighborhood safety parameters.

Additionally or alternatively, one or more application programs 119 used by the sensing system 101 may include computer-executable instructions for using image, text, and/or natural language processing to generate assessments of various parameters of neighborhood safety using filed insurance claims, crime reports, suspicious activity reports, property damage reports, etc. Neighborhood safety assessments may be used to determine or update various insurance conditions (e.g., rates, adjustments, incentives, and the like) or quantify an effect on property prices in a neighborhood.

The systems described herein may be used by an insurance provider, real estate organization, financial institution or other entity to better assess the safety profile of a neighborhood. The systems and methods described herein may be used by or with other entities or types of entities and/or for other purposes without departing from the invention.

Figure 2:
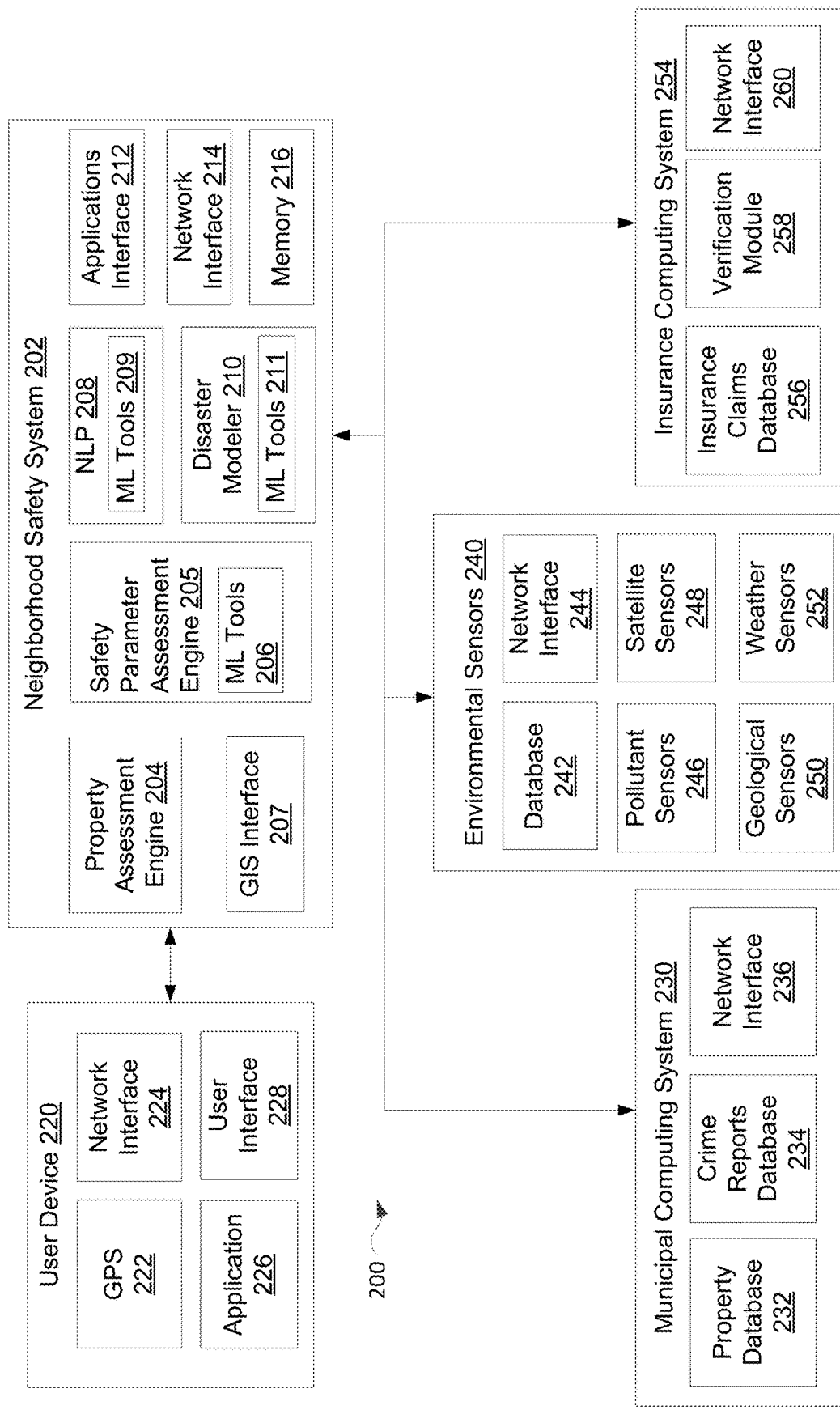
FIG. 2 is a schematic diagram of example computing systems according to one or more aspects described herein.

FIG. 2 is a schematic diagram of example computing systems used for generating an assessment of neighborhood safety parameters using sensors, according to one or more aspects described herein.

On a high level, the example computing systems may include but are not limited to, a user device 220, one or more systems or servers for receiving requests for and generating assessments and other analytics of neighborhood safety parameters ("neighborhood safety system" 202), one or more systems or servers used by municipal office 151 (e.g., "municipal computing system" 230), one or more systems or servers used by insurance office 161 (e.g., "insurance computing system 254"), and a plurality of devices, systems, or servers used for or facilitating the sensing of environmental data (e.g., "environmental sensors" 240). As shown in FIG. 2, network interfaces 214, 224, 236, 244, and 260 may enable communications between the various systems over a wireless network, wired network, or any other desired network. The network interfaces may comprise circuitry needed to communicate with other systems over a network. One or more of the systems shown in FIG. 2 may be based on system 101 in FIG. 1 or include one or more components of system 101 in FIG. 1. For example, the neighborhood safety system 202 may include one or more processors and a memory. Furthermore, the neighborhood safety system 202 may host, run, or manage one or more programs, software, websites, or applications, e.g., via an application interface 212. Also or alternatively, the user device 220 may run an application 226 (e.g., "neighborhood safety application") that is hosted or managed by the neighborhood safety system 202.

At a high level, a user may inquire to know the safety profile of a geographical area ("desired area"). For example, a prospective mover may want to know how safe a neighborhood is before making a decision to buy a property in the neighborhood. The user, via user device 220, may send a request to the neighborhood safety system 202 to assess the safety of the desired area. The safety of a desired area may be assessed via a plurality of safety parameters, as will be discussed further herein. Each safety parameter may have a characteristic or value. After receiving the request, the neighborhood safety system 202 may query external systems or devices for relevant information to assess the safety of the desired area. The external systems or devices may be based on sensors and/or offices based in the desired area. For example, the external systems or devices may include, but are not limited to, the environmental sensors 240, the municipal computing system 230, the insurance computing system 254, etc. The neighborhood safety system 202 may be remotely located from, or be local to, the neighborhood or the desired area for safety assessment. In some aspects, the neighborhood safety system 202, can be the same as or otherwise associated with the insurance computing system 254.

After receiving a request for an assessment of a safety parameter for a neighborhood or desired area, the neighborhood safety system 202 may use a module, application, software, code, or interface to determine the geographic location of the neighborhood or the desired area. As shown in FIG. 2, the neighborhood safety system may comprise a geographic information system (GIS) interface 207, which may enable the neighborhood safety system 202 to capture, store, manipulate, analyze, manage, and present geographical data, e.g., of the neighborhood or desired area for which a safety parameter is requested to be assessed. Furthermore, the GIS interface may be used to present assessments of various safety parameters visually, e.g., via labels and/or markers overlaid on a map of the neighborhood or desired area. Also or alternatively, the neighborhood safety system 202 may automatically find out the location of the desired area for which a safety parameter is requested to be assessed by tracking the user device's location. User device's location can be tracked, for example, by a global positioning system (GPS) 222 in the user device 220. In other aspects, the request to generate an assessment of a safety parameter may include locational information of the neighborhood or desired area (e.g., name of the neighborhood, zip code, radial vicinity, address, etc.) The neighborhood safety system may use information pertaining to the location of the neighborhood or desired area to search for and establish connections with external systems located in or servicing the neighborhood or desired area (e.g., municipal computing system 230, environmental sensors 240, insurance computing system 254, etc.).

The neighborhood safety system 202 may comprise various data or storage engines to create, read, update, and/or delete data from its memory 216. These engines may include, for example, safety parameter assessment engine(s) 205 and a property assessment engine 204. As was described in conjunction with memory 115 in FIG. 1, memory 216 of the neighborhood safety system 202 may include volatile and non-volatile memory, and short term storage. Various information received from external systems (e.g., user device 220, municipal computing system 230, environmental sensors 240, and insurance computing system 254) may be stored in memory 216. Using relevant information pertaining to a safety parameter that may be received from external system(s) and stored in memory 216, a safety parameter engine may assess the safety parameter. A safety parameter may be an aspect of a neighborhood that is associated with its safety, peacefulness, and/or stability. For example, safety parameters may include, but are not limited to weather events (e.g., storm, flood, etc.), geological events (e.g., earthquakes), environmental (e.g., air pollution, water pollution, etc.), crime, terrain (e.g., mud slides, sinkholes, risks of falling due to uneven terrains, etc.), fire, disease, etc.

The assessment of the safety parameter may involve the safety parameter assessment engine 205 determining a quantifiable and/or qualitative characteristic, value, property, and/or description for the safety parameter. For simplicity, the characteristic, value, property, and/or quality may be referred to as "characteristic and/or value," "parameter characteristic and/or value," and/or "safety parameter characteristic and/or value." Thus, a characteristic and/or value for geological events, environmental, and/or weather related safety parameters may include, but is not limited to, a pollutant level, an indication of a weather event or upcoming weather event (e.g., temperature, barometer reading, humidity level, etc.), a seismograph reading, etc. A characteristic and/or value of a safety parameter related to disease may include an indication of a microbe or disease presence (e.g., cell or antigen count); a concentration or count of doctors, medical facilities, or pharmacies in the desired area; etc. A characteristic and/or a value for a safety parameter related to crime may include, for example, the number or frequency of incidents of a criminal activity (e.g., kidnapping, burglary, robbery, homicide, battery, assault, larceny, bullying, money laundering, cybercrime, etc.). Characteristics and/or values for a safety parameter related to fire may include incidents, frequency, or severity of fires, arson, wildfires, etc. Characteristics and/or values for a safety parameter related to terrain may include a measurement of the relative evenness or flatness of a terrain; a number of incidents of, a frequency of, or a severity of mud slides, sinkholes, avalanches, or other terrain-related events; etc.

The safety parameter assessment engine 205 may utilize various machine learning based tools 206 to generate an assessment of a safety parameter, based on received information of the characteristics and/or values of the safety parameter. For example, if a user were to request an assessment of weather related events (a safety parameter) for a specific neighborhood, the neighborhood safety system 202 may receive current temperature, precipitation, air pressure, and humidity data from weather sensors 252, but also stored temperature, precipitation, air pressure, and humidity data from the past. The safety parameter assessment engine 205 may input the data into a trained machine learning algorithm to forecast weather trends in the future, and assess the safety based on the forecasted weather trends. The trained machine-learning algorithm may be stored as an ML tool 206 and/or within memory 216. Furthermore, the safety parameter assessment engine 205 may use characteristics and/or values for a safety parameter to predict or model a disaster or catastrophe. In some aspects, a module, plug-in, software, and/or code (e.g., "disaster modeler" 210) may enable the safety parameter assessment engine 205 to model or predict the development of, onset of, severity of, and/or damage caused by the disaster or catastrophe. The disaster modeler 210 may also use various machine learning based tools 211 to predict or model a disaster or catastrophe based on training data or trained machine-learning algorithms that use characteristics and/or values of a safety parameter.

In fulfilling requests to generate assessments for a safety parameter, the neighborhood safety system 202 may establish connections with external systems, such as municipal computing system 230 and insurance computing system 254, e.g., via network interfaces 214, 236, and 260. From such systems, the neighborhood safety system 202 may receive information that involves natural language entries. For example, in order to assess the crime of a neighborhood, the neighborhood safety system 202 may receive crime reports of crimes that have occurred in the neighborhood over a preselected duration of time. The crime reports may be received digitally from the municipal computing system 230, e.g., from a crime reports database 234. However, the digitized crime reports may nevertheless be in the form of a natural language input (e.g., "On Sep. 1, 2010, Neighborhood Grocery was robbed, resulting in $10,000 loss in business."), and the characteristics and/or values of a safety parameter (e.g., crime) may not be as apparent to the neighborhood safety system 202.

In another example, in order to assess safety parameters, the neighborhood safety system 202 may receive insurance claims filed over a preselected duration of time. The insurance claims may be submitted or filed by property owners or renters, business owners or renters, vehicle owners or renters, and the like, who reside, do business in, or otherwise have an interest in the neighborhood or desired area. The insurance claims may have been submitted and/or filed at an insurance provider office or agency. The insurance computing system 254 associated with the insurance provider office or agency may have verified the insurance claims, e.g., via a verification module 258, and stored the verified insurance claims, e.g., in an insurance claims database 256. The neighborhood safety system 202 may electronically receive the insurance claims from the insurance computing system 254. However, the electronically received insurance claims may nevertheless be in the form of a natural language input (e.g., "On Sep. 1, 2010, Neighborhood Grocery owner Bob requests compensation of a loss suffered in the amount of $10,000 as a result of a robbery"). Consequently, the characteristics and/or values of a safety parameter (e.g., crime) may not be as apparent to the neighborhood safety system 202. In some aspects, and to overcome the above-described issues, the neighborhood safety system 202 may include a natural language processor (e.g., "NLP" 208) to process the received natural language input.

The NLP 208 may be a subsystem, software, plug-in, application, or code that may include various processors (e.g., pre-processors, post-processors, etc.), libraries, and/or AI-based systems (e.g., machine learning (ML) tools 209) to analyze and convert natural language to one that could result in a computing system 202 to perform substantive functions. The substantive functions may include identifying, creating, replacing, updating, and/or deleting a characteristic and/or value for a safety parameter. A library and AI-based tools (e.g., ML tool 209) may guide the NLP 208 for various uses in natural language processing, including the undergoing of supervised and unsupervised learning from language data. The library may be a repository, look-up table, and/or database and may be located within memory 216. Together with the library, the ML tool 209 may support common NLP tasks, such as tokenization, sentence segmentation, part-of-speech tagging, named entity extraction, chunking, parsing, and coreference resolution. These tasks may be needed to build more advanced text processing services. The ML tool 209 may also include maximum entropy and perceptron based machine-learning tools.

In some aspects, the neighborhood safety system may use an assessment of a safety parameter to determine its quantitative effect on other aspects of the neighborhood or desired area. For example, a user seeking to sell a property in the neighborhood may desire to know what effect the safety profile of the neighborhood would have on the property value of the property that the user is seeking to sell. Various algorithms for and/or computer executable instructions for property valuation, may be stored in memory 216. Furthermore, the neighborhood safety system 202 may receive property information (e.g., existing property values, property details, etc.) from the municipal computing system 230, which may store property information of properties in the neighborhood or desired area, e.g., in property database 232. The property assessment engine 204 may use an assessment of a safety parameter, stored computer executable instructions and algorithms related to property valuation, and received property information to quantify the effect of a safety parameter on a property value.

Based on the requests received from the user device 220, the neighborhood safety system 202 may apply assessments of neighborhood safety parameters in other aspects. For example, the neighborhood safety system 202 may quantify the effect of an assessment on an insurance condition (e.g., rates, adjustments, incentives, and the like). In some aspects, an assessment of a safety parameter may be used to update an insurance policy of a user. For example, if the user were to reside in, work in, or otherwise be associated with the neighborhood or desired area for which the neighborhood safety system 202 has generated a safety assessment, the neighborhood safety system may be used to update the user's insurance policy. This aspect may occur, for example, where the neighborhood safety system 202 is utilized by the user's insurance provider or is an extension of the insurance computing system 254.

The neighborhood safety system 202, e.g., via its safety parameter assessment engine 205, may aggregate and/or holistically evaluate assessments of individual safety parameters of a neighborhood or desired area to determine an overall or comprehensive safety assessment. For example, the overall or comprehensive safety assessment may be an amalgamation of assessments of individual safety parameters. Also or alternatively, where assessments of individual safety parameters involve a quantitative score, the overall or comprehensive safety assessment may be a total score or a weighted average (e.g., mean, median, etc.) of individual scores.

User device 220 may comprise, for example, a cell phone, smartphone, tablet (e.g., with cellular transceivers), laptop (e.g., communicatively coupled to cellular transceivers), desktop, wearable devices (e.g., smart watches, electronic eye-glasses, etc.), or other types of computing devices configured to communicate with the neighborhood safety system e.g., over a network via network interface 224. The user device 220 may be associated with a user who desires to know the safety of a neighborhood or desired area. The user device 220 may directly or indirectly transmit or receive information to the neighborhood safety system 202. For example, the user device may run an application, program, or software (e.g., 226), or display a website. The application, program, software or website may be managed, created, or hosted by the neighborhood safety system 202, e.g., via application interface. Furthermore, the user device 220 may comprise a user interface 228 to allow the user to view displayed contents of the application 226, or enter input, e.g., via a keyboard, keypad, touch screen, mouse, etc. For example, a user may enter a request to generate an assessment of a safety parameter via the user interface 228, and this request may be sent to the neighborhood safety system 202. Furthermore as described above, the user device 220 may have an internal geographical tracking device (e.g., a global positioning system (GPS) 222). The GPS 222 may be used to automatically determine a neighborhood or a desired area for a request for an assessment of a safety parameter, if the neighborhood or the desired area is at the user device's present location. The user device 220 may be configured in a similar manner as terminal 171 and/or system 101 of FIG. 1.

The municipal computing system 230 may be comprised of a property database 232, a crime reports database 234, and a network interface 236. In some aspects, in addition to or as an alternative to the municipal computing system 230, there may be a plurality of computing systems that collectively store relevant information pertaining to individuals or property of a municipality, and which could be used to assess the safety of a neighborhood or a desired area. For example, a computing system of a police station may store crime reports, e.g., in a crime reports database 234, and a computing system of a local tax collections office may store information pertaining to a plurality of properties of a neighborhood or desired area, e.g., in a property database 232.

The plurality of environmental sensors 240 may include, but are not limited to sensors that measure a pollutant (e.g., pollutant sensors 246), sensors placed on a satellite or drone (e.g., satellite sensors 248), geological sensors 250 (e.g., seismographs), and weather sensors 252 (e.g., thermometer, barometer, wind vanes, anemometer, optical sensors, humidity sensors, etc.). The individual environmental sensors need not be located at the same place. For example, while the neighborhood or desired area may have a weather sensor 252, the nearest pollutant sensor 246 or geological sensor 250 may be at the center of the metropolitan area of the neighborhood or of the desired area.

The insurance computing system 254 may be comprised of an insurance claims database 256, a verification module 258, and a network interface 260. As discussed above, the insurance computing system 254 may be a computing system or systems that store filed and/or verified insurance claims of users, workers, or property owners located in the neighborhood and/or desired area of the requested safety assessment. The computing system or systems may be of an insurance office, insurance agency, insurance provider, etc. In some aspects, the insurance claims database 256 may categorize filed and unverified insurance claims, verified insurance claims, and/or compensated insurance claims. The verification process may be performed by a module, program, software, or algorithm for assessing an insurance claim and confirming that there is no fraudulent information, e.g., by the verification module 258. The insurance claims may be based on a claim for compensation for a damage or loss incurred. The damage or loss may indicate an aspect of a safety parameter. For example, a user may file an insurance claim for loss caused by a robbery, which may indicate a prevalence of crime in a neighborhood. In another example, a user may file an insurance claim for damage caused by a hurricane, which may indicate a prevalence of catastrophic weather events in a neighborhood.

Figure 3:
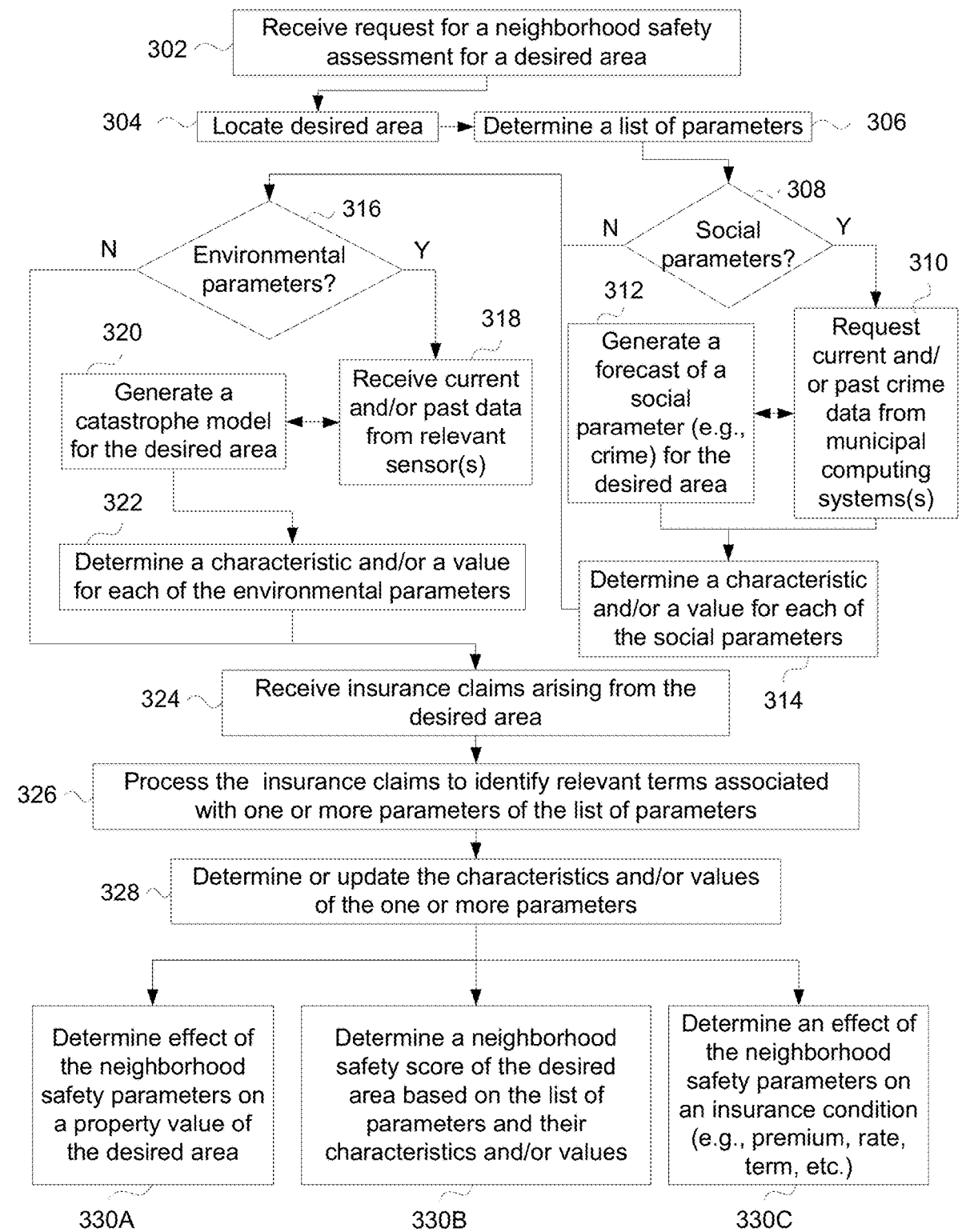
FIG. 3 is a flow chart illustrating one example method of generating an assessment of neighborhood safety parameters using sensors, according to one or more aspects described herein.

FIG. 3 is a flow chart illustrating one example method of generating an assessment of neighborhood safety parameters using sensors, according to one or more aspects described herein. One or more steps shown in FIG. 3 may be performed by the neighborhood safety system 202 of FIG. 2 and/or system 101 of FIG. 1.

At step 302 the neighborhood safety system 202 may receive a request to assess neighborhood safety based on a plurality of safety parameters (e.g., a request for a "neighborhood safety assessment") for a desired area or neighborhood. The request may be sent by the user via user device by inputting the request, via clicking icons or other functionalities on the user interface, natural language input via text and/or audio, or the like. An application associated with the neighborhood safety system 202, and running on the user device may enable the user to send the request. The request may be specify, a geographic area for which a safety assessment is requested (e.g., "desired area"). The desired area may be a vicinity based on a point on a visual map; a vicinity based on an address; an enclosed area on a map; an identifier of a neighborhood, town, village, city, zip code, etc. The vicinity may be inputted based on a desired radius span or proximity from a selected location. In some aspects, e.g., where the user has not explicitly indicated in the request, the desired area may be deemed to be in a vicinity (e.g., radius span) of the user device 220, and located, e.g., using a GPS 222 of the user device 220. The request may further include a list of safety parameters on which to base the requested neighborhood safety assessment. In at least one aspect, safety parameters may be broadly categorized into environmental safety parameters ("environmental parameters") and social safety parameters ("social parameters").

Thus, based on the received request, the neighborhood safety system 202 may locate the desired area or neighborhood (e.g., as in step 304), and identify or determine the list of safety parameters on which the assessment is based (e.g., as in step 306). Environmental parameters may include, but are not limited to safety parameters of weather factors or events (e.g., rain, ice, flood, snow, storms, blizzards, hurricane, tornado, avalanche, gust, heat wave, polar vortex, wind chills, freezes, humidity, etc.), geological factors or events (e.g., terrains (e.g., hilliness), mudslides, sinkholes, earthquakes, volcanoes, etc.), and pollution factors or events (e.g., particulates, carbon monoxide, pollen, hay, dust, air pollutants, water pollutants, haze, chemical spill, etc.). Social parameters may include, but are not limited to, crime, unrest, disease (e.g., presence of, levels of, etc.), or the like. In some aspects, environmental parameters may be assessed based on data obtained from environmental sensors that may indicate characteristics and/or values for the environmental parameter.

If the list of parameters include social parameters (e.g., step 308=Y), the neighborhood safety system 202 may request current and/or past social parameter data from the municipal computing system 230 (e.g., as in step 310). The data may indicate characteristics and/or values of the social parameter. For example, the neighborhood safety system 202 may request current and/or past crime data from the local police computing systems, for crimes committed in the desired area. The past data may be based on a predefined duration of time in the past. In some aspects, the neighborhood safety system 202 may use the current and/or past data to generate a forecast of the social parameter for the desired area. For example, the neighborhood safety system may generate a crime forecast for the desired area (e.g., as in step 312). The forecasting may be performed using ML tools 206. The forecast may be presented to the user via user device, e.g., based on demand or accompanied with the neighborhood safety assessment. As used herein, crimes may include, for example, any unlawful human activity that may affect the safety of others, e.g., assault, battery, kidnapping, robbery, homicide, rape, larceny, cybercrime. In some aspects, a safety parameter and an assessment of the safety parameter may refer to one or more of these crimes.

At step 314, the neighborhood safety system 202 may determine a characteristic and/or a value for each of the listed social parameters. For example, if the request for a neighborhood safety assessment was based on crime, the characteristics and/or values may include, e.g., a number of incidences of the crime, a severity of the crime, a severity of each incidence, a frequency of the incidence of the crime, a damage caused by each incidence of the crime, a loss suffered from each incidence of the crime, etc. The characteristics and/or values may be quantified or otherwise digitized and stored into memory 216. For example, an indication of severity may be quantified (e.g., 1=least severe, 10=most severe).

Subsequently, or if the list of parameters does not include social parameters, the neighborhood safety system 202 may determine whether the list of parameters includes environmental parameters (e.g., as in step 316). In some aspects, the determining of whether the list of parameters includes environmental parameters may be prior to, simultaneously with, or subsequent to the determining of whether the list of parameters includes social parameters.

Figure 4:
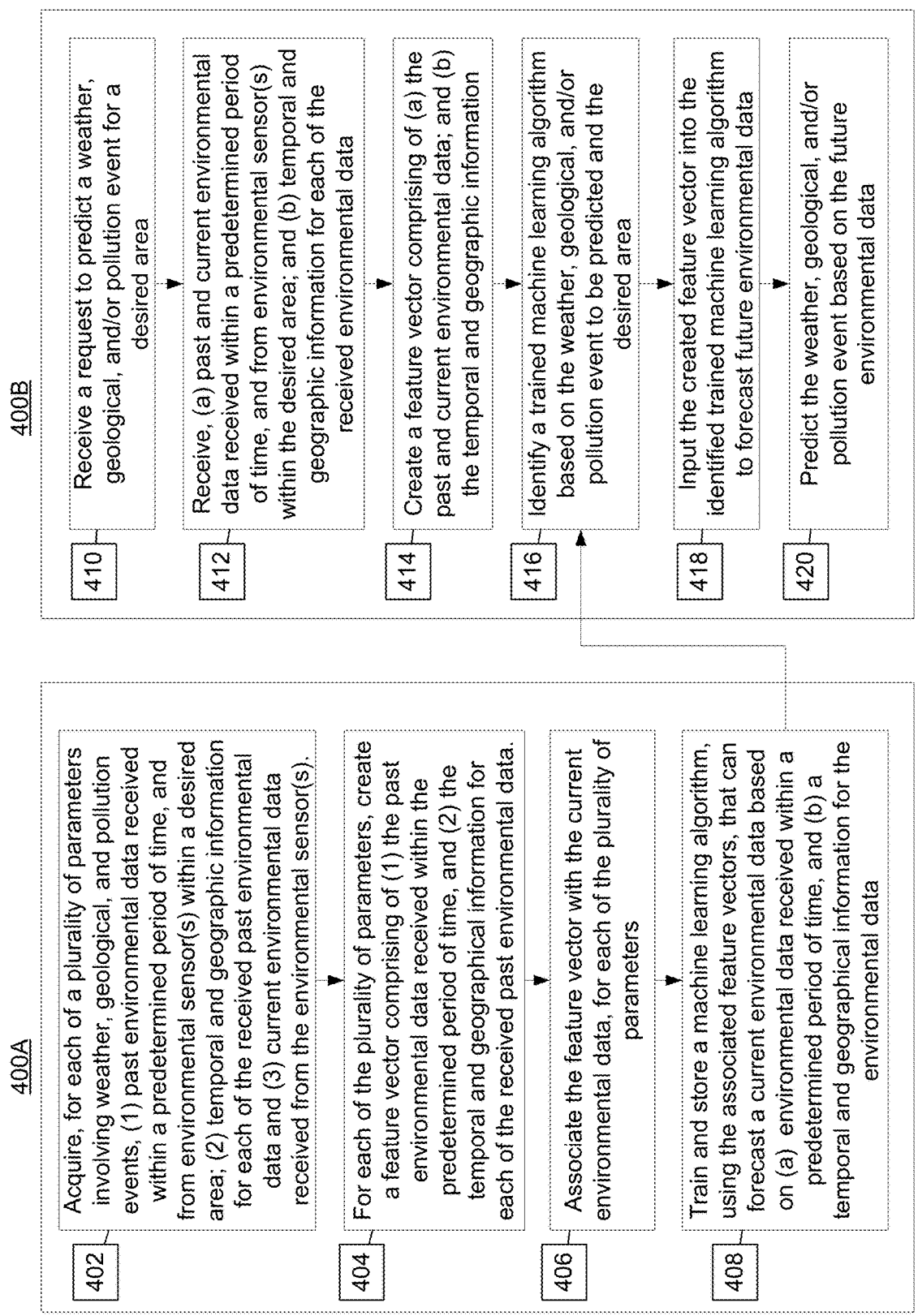
FIG. 4 is a flow chart illustrating one example method of using machine learning to generate an assessment of neighborhood safety parameters involving weather, geological, and/or pollution events, according to one or more aspects described herein.

If the list of parameters includes environmental parameters (e.g., step 316=Y), the neighborhood safety system 202 may request current and/or past environmental parameter data from the relevant environmental sensor(s) 240 and/or from their respective or collective storage 242 (e.g., as in step 318). The data may indicate characteristics and/or values of the environmental parameter on which the neighborhood safety assessment is requested to be based. For example, the neighborhood safety system 202 may request current and/or past weather data from the local weather sensors 252, for weather related measurements in the desired area. The past data may be based on a predefined duration of time in the past (e.g., last five years). In some aspects, the neighborhood safety system 202 may use the current and/or past data to generate a forecast of environmental parameter data for the desired area (e.g., as in step 320). For example, the neighborhood safety system 202 may generate a weather forecast for the desired area, and predict weather events or disasters that may affect neighborhood safety. The weather forecasting and/or disaster modeling may be performed using safety parameter assessment engine 205, disaster modeler 210 or their respective ML tools 206 and 211. FIG. 4 depicts a flow chart of at least one method of forecasting and predicting environmental events for a desired area. The forecast or disaster model may be presented to the user via user device, e.g., based on the user's demand or as an accompaniment with the neighborhood safety assessment.

At step 322, the neighborhood safety system 202 may determine a characteristic and/or a value for each of the listed environmental parameters. For example, if the request for a neighborhood safety assessment was based on weather, the characteristics and/or values may include, e.g., a temperature, a barometer reading, a humidity level, a flood depth, a wind speed, a description of the weather (e.g., cloudy, sunny, windy, etc.) etc. The characteristics and/or values may be quantified or otherwise digitized and stored into memory 216. For example, a description of the weather may be quantified based on cloud cover (e.g., 1=sunny/clear, 10=most cloudy), or digitized based on binary true statements (e.g., precipitation=1 and no precipitation=0).

In some aspects, the characteristics and/or values of safety parameters other than environmental parameters and social parameters may be determined, e.g., by establishing connections with and receiving data from the appropriate relevant systems. It is contemplated that the list of parameters on which the neighborhood safety assessment is based need not be limited to one or both of environmental parameters or social parameters, and may be entirely comprised of parameters other than environmental parameters or social parameters. Furthermore, the request for the neighborhood safety assessment need not indicate a list of safety parameters on which to base the neighborhood safety assessment. In some examples, the request may be based on a predetermined default set of safety parameters or may be based on a comprehensive list of safety parameters, and/or may be based on a holistic safety parameter.

Furthermore, the neighborhood safety system 202 may utilize insurance based information to determine or update further characteristics and/or values of safety parameters for the neighborhood safety assessment. Thus, at step 324, the neighborhood safety system 202 may receive insurance claims for losses incurred by properties or individuals in the desired area. The insurance claims may be received from the insurance computing system 254. The insurance claims may be verified or otherwise vetted to confirm they are not fraudulent or frivolous, e.g., by verification module 258, and/or by the neighborhood safety system 202 upon receipt. The insurance computing system may be located and a request may be sent to it, based on a determination of the insurance office or provider that services properties and/or individuals in the desired area. For example, customer data for the insurance offices or providers, property data for the insurance offices or providers, or information pertaining to the geographic regions of insurance offices or providers may be stored in memory 216. Based on the desired area, the neighborhood safety system 202 may send requests for insurance claims from the relevant insurance computing system 254. Also or alternatively, the insurance computing system 254 may be a centralized computing system that stores records of insurance claims from various insurance providers, and maps the insurance claims to various geographic points, including those in the desired area.

The insurance claims, however, may not necessarily be in a format that a computing system may use to identify, determine, or update characteristics and/or values for various safety parameters. The insurance claims may be in a natural language format. For example, an insurance claim may read: "On Sep. 1, 2010, Neighborhood Grocery owner Bob requests compensation of a loss suffered in the amount of $10,000 as a result of a robbery". Consequently, the characteristics and/or values of a safety parameter (e.g., crime) may not be as apparent to the neighborhood safety system 202. Thus, at step 326, the neighborhood safety system 202 may process the insurance claims to identify relevant terms associated with one or more parameters of the list of parameters. A natural language processor (e.g., "NLP" 208) of the neighborhood safety system 202 may process the received natural language input to identify, create, replace, update, and/or delete a characteristic and/or value for a safety parameter of the listed safety parameters. Furthermore, AI-based tools (e.g., ML tool 209) and any libraries for the AI-based tools stored in memory 216 may guide the NLP 208 in the natural language processing, including the undergoing of supervised and unsupervised learning from language data to determine relevant terms associated with one or more safety parameters. It is possible that the received insurance claims and their processing may result in new safety parameters or new characteristics and/or values for existing or new safety parameters. Depending on user preferences laid out in the request for neighborhood safety assessment or system settings, the new safety parameters and/or new characteristics and/or values may be considered in the neighborhood safety assessment. Thus, new safety parameters could be added to the list of safety parameters determined in step 306. Also or alternatively, at step 328, using the processed insurance claims, the neighborhood safety system 202 may determine or update the characteristics and/or values of one or more parameters from the list of parameters identified in step 306.

Depending on the user request or preferences with respect to the neighborhood safety assessment, and/or depending on system settings, the determined or updated characteristics and/or values for the list of safety parameters can be utilized in various ways. An individual score or assessment for each safety parameter may be determined and presented to the user, via an application 226 and/or a user interface 228 of the user device 220. Also or alternatively, the individual scores or assessments can be aggregated, summed up, and/or summarized. For example, as shown in step 330B, the neighborhood safety system 202 may determine a neighborhood safety score of the desired area based on the list of safety parameters and their characteristics and/or values. The neighborhood safety score may be a total score or assessment based on the individual scores or assessments, and may be presented to the user, via an application 226 and/or a user interface 228 of the user device 220. As will be discussed below, FIG. 5 displays an example of at least one such total score or assessment.

In some aspects, the neighborhood safety system 202 may determine the effect of the neighborhood safety parameters on a property value of the desired area (e.g., as in step 330A). For example, an individual assessment or score for the neighborhood safety parameter of crime could be used to determine a quantitative effect on a property in the desired area (e.g., an amount r percent drop in home value). Based on the located desired area (e.g., from step 304), the neighborhood safety system 202 may determine (e.g., via requesting data from municipal computing systems 230 or by retrieving from memory 216) property data of properties known to be within the desired area. The property data may include property values for a given (e.g., current) year. The neighborhood safety system 202 may utilize external market data that show drops in property values due to increases in crime and other safety parameters to learn relationships between safety parameters and property values. The learning may be applied to the properties of the desired area and the safety parameter data of the desired area to determine the corresponding drop in value.

Furthermore, the neighborhood safety system 202 may determine an effect of the neighborhood safety parameters on an insurance condition for an individual or property associated with the desired area. The individual may own property, rent, and/or work in the desired area, and the property (e.g., car, home, commercial establishment, business, etc.) may be located in or be used in the desired area. For example, an individual seeking to purchase a new home in the desired area, who requests a neighborhood safety assessment may also need home or auto insurance. The neighborhood safety assessment, which may be unfavorable due to safety parameters of weather or crime, could be used to automatically update and/or determine the conditions of the individual's home or auto insurance. The insurance conditions for example, an insurance premium, an insurance rate, an insurance term, a deductible, etc.

FIG. 4 is a flow chart illustrating one example method of using machine learning to generate an assessment of neighborhood safety parameters involving weather, geological, and/or pollution related events, according to one or more aspects described herein. Furthermore, one or more steps shown in FIG. 4 may be used to determine future characteristics and/or values of a safety parameter, e.g., geological, weather, and/or pollutant events. For ease and simplicity, characteristics and/or values of safety parameters such as geological events, weather events, and pollution may be referred to as "environmental data."

The method depicted in FIG. 4 may include a training method 400A for training one or more machine learning algorithms based on, e.g.: past environmental data received within a predetermined period of time; temporal and geographic information for each of the received past environmental data and current environmental data received from the environmental sensor(s). The past environmental data and current environmental data may be received from environmental sensors in the neighborhood or desired area for which a forecasting of future environmental data is requested. The method depicted in FIG. 4 may also include a production method 400B for using the trained machine learning algorithm to predict a weather, geological, and/or pollution related event. Methods 400A and 400B may be performed by the neighborhood safety system 202, e.g., via safety parameter assessment engine 205, disaster modeler 210, or via their respective ML tools 206 and 211. Alternatively, the training method (e.g., 400A) may be performed by an external server or computing system (e.g., an AI or research lab). In some implementations, a trained machine learning algorithm may be retrieved by the neighborhood safety system 202 to determine future environmental data and/or predict a weather, geological, and/or pollution event, e.g., in method 400B.

Thus, step 402 may include acquiring, for each of a plurality of parameters involving weather, geological, and/or pollution, a training data set for the machine learning algorithm to be trained. The training data set may include, but is not limited to: past environmental data received within a predetermined period of time; (2) temporal and geographic information for each of the received past environmental data and (3) current environmental data received from the environmental sensor(s). The past environmental data and current environmental data may be received from environmental sensors in the neighborhood or desired area for which a forecasting of future environmental data is requested.

In some implementations, the environmental data may be obtained by establishing a connection with the appropriate environmental sensors 240 (e.g., pollutant sensors 246, geological sensors 250, weather sensors 252, etc.). The nearest environmental sensors may be located based on the desired area or neighborhood that is requested to be assessed. Furthermore, geographical and temporal data may be received from the environmental sensors 240, e.g., via a timestamp of when the environmental data was gathered by the environmental sensor, and the location of the environmental sensor (e.g., longitude and latitude, distance from user, distance from the desired area or neighborhood, etc.). For example, the temporal information may involve the date and time at which the environmental data was obtained (e.g., sensed), and the geographic information may refer to a point or location within the desired area or the neighborhood in which a request for a safety assessment has been made. For past environmental data, the neighborhood safety system 202 may access stored data (e.g., database 242 of environmental sensors 240).

Step 404 may involve creating feature vectors for each of the plurality of parameters. In some aspects, there may be a feature vector created for each location point in the desired area or neighborhood at which the environmental data was measured. The feature vector may include, for example: (1) the past environmental data received within the predetermined period of time, and (2) the temporal and geographical information for each of the received past environmental data. Each of these features may be quantified and/or may be expressed as mathematical functions. At step 406, the feature vectors may be associated with the current environmental data, for each of the plurality of parameters. As discussed above, there may be a feature vector for every point or location in the desired area or neighborhood where there is a past environmental data and a corresponding current environmental data.

Step 408 may include training a machine learning algorithm using the associated feature vectors. The resulting machine learning algorithm would be one that can forecast environmental data (e.g., current environmental data based on past environmental data) for a plurality of parameters based on (a) environmental data received within a predetermined period of time, and (b) a temporal and geographical information for the environmental data. Thus, the training in the above described aspect involves learning the relationship between past environmental data (e.g., environmental data received within a predetermined period of time) in a geographic area and the environmental data at a designated time (e.g., current time) in a geographic area. However, the designated time need not be at the current time. For example, as will be discussed in the application phase 400B, the trained machine-learning algorithm may be used to predict environmental data for a designated time in the future, based on inputted environmental data comprising of past environmental data and current environmental data. Furthermore, the geographic area and the points of location within it need not be the neighborhood or desired area for which there is the request for the safety assessment.

The training of the machine-learning algorithm may involve supervised learning between a domain (e.g., the feature vectors) and a range (e.g., the current environmental data). Examples of machine learning algorithms may include, but are not limited to multi-layer perceptron, neural networks, support vector machines, linear regression, logistic regression, decision tree learning, or a combination thereof.

The training method 400A may then save the results of the machine learning algorithm, including feature weights, in a memory of the neighborhood safety system 202, e.g., memory 216. Alternatively or additionally, an external computing system or server (e.g., a research lab) may save the trained machine-learning algorithm, which can be retrieved to be used by the neighborhood safety system 202 for production method 400B. The stored feature weights may define the extent to which a geographical or temporal factor or a specific type of environmental data affects the current environmental data at a given location and a given time (e.g., current time).

Referring to production method 400B, step 410 may include receiving a request to predict a weather, geological, and/or pollution event for a desired area. The request may be inputted by the user into the user device 220 via application 226 and/or user interface 228. For example, as explained in conjunction with FIG. 3, the user may want to know more about an assessment of the safety parameter related to weather, geological, and/or pollution events, and would like to visually understand the probability that a hurricane could occur within the next twelve months in a given neighborhood. The user, via user device 220, may submit a request to forecast the next hurricane to the neighborhood safety system 202. The neighborhood safety system may use past and/or present environmental data gathered for the given neighborhood and a trained machine-learning algorithm based on methods presented herein. Also or alternatively, in the process of making an assessment for a safety parameter involving weather, geological, and/or pollution events, the neighborhood safety system 202 may factor in any forecasted weather, geological, and/or pollution events, and may therefore utilize the methods presented herein. As such, the request to predict the weather, geological, and/or pollution event for the desired area may be a signal to the safety parameter assessment engine 205 and/or to the disaster modeler 210 (e.g., to their respective ML tools 206 and 211).

At step 412, the neighborhood safety system 202 (e.g., at the ML tool at the safety parameter assessment engine 205 and/or at the disaster modeler 210) may receive (a) past and current environmental data received within a predetermined period of time, and from environmental sensor(s) within the desired area; and (b) temporal and geographic information for each of the received environmental data. As discussed above, the temporal information may involve the date and/or time at which the environmental data was obtained (e.g., sensed), and the geographic information may refer to a point or a location within the desired area or the neighborhood in which a request for a safety assessment has been made. Step 414 may include creating a feature vector comprising of (a) the received environmental data (e.g., the past and current environmental data received within a predetermined period of time, and from environmental sensor(s) within the desired area); and (b) temporal and geographic information for each of the received environmental data.

At step 416, the neighborhood safety system 202 may identify a trained machine learning algorithm for the requested weather, geological, and/or pollution event to be forecasted and the desired area or neighborhood. For example, the neighborhood safety system 202 may search for and retrieve (e.g., from memory 216 and/or ML tools 206 or 211) a trained machine learning algorithm for predicting the event that is requested by the user (e.g., weather, geological, and/or pollution event). For example, some trained machine learning algorithms may have used a training data set comprising mostly of pollutant emissions data, and would be better at forecasting a possible pollution related haze event of a neighborhood. Some trained machine learning algorithms may have relied on a training data comprising weather related measurements (e.g., precipitation levels, temperatures, etc.), and may be better equipped at predicting a weather event. In some implementations, the neighborhood safety system 202 may identify a trained machine-learning algorithm from external computing systems and/or servers. After identification and retrieval, the neighborhood safety system 202 may input the created feature vector into the identified trained machine-learning algorithm (e.g. as in step 418). Based on the training in method 400A, the trained machine-learning algorithm may output the future environmental data, in accordance with the request. The date and/or time in the future for the future environmental data may be based on any temporal constraints applied in the request.

From the future environmental data, the neighborhood safety system 202 may forecast the weather, geological, and/or pollution event (e.g., as in step 420). For example, if future environmental data shows severe precipitation and wind speed of 160 miles per hour, the neighborhood safety system 202 may identify such future environmental data as the weather event of a category 5 hurricane. In some implementations, the training method 400A and/or the production method 400B may be performed by the safety parameter assessment engine 205 or disaster modeler 210 of the neighborhood safety system 202.

Figure 5:
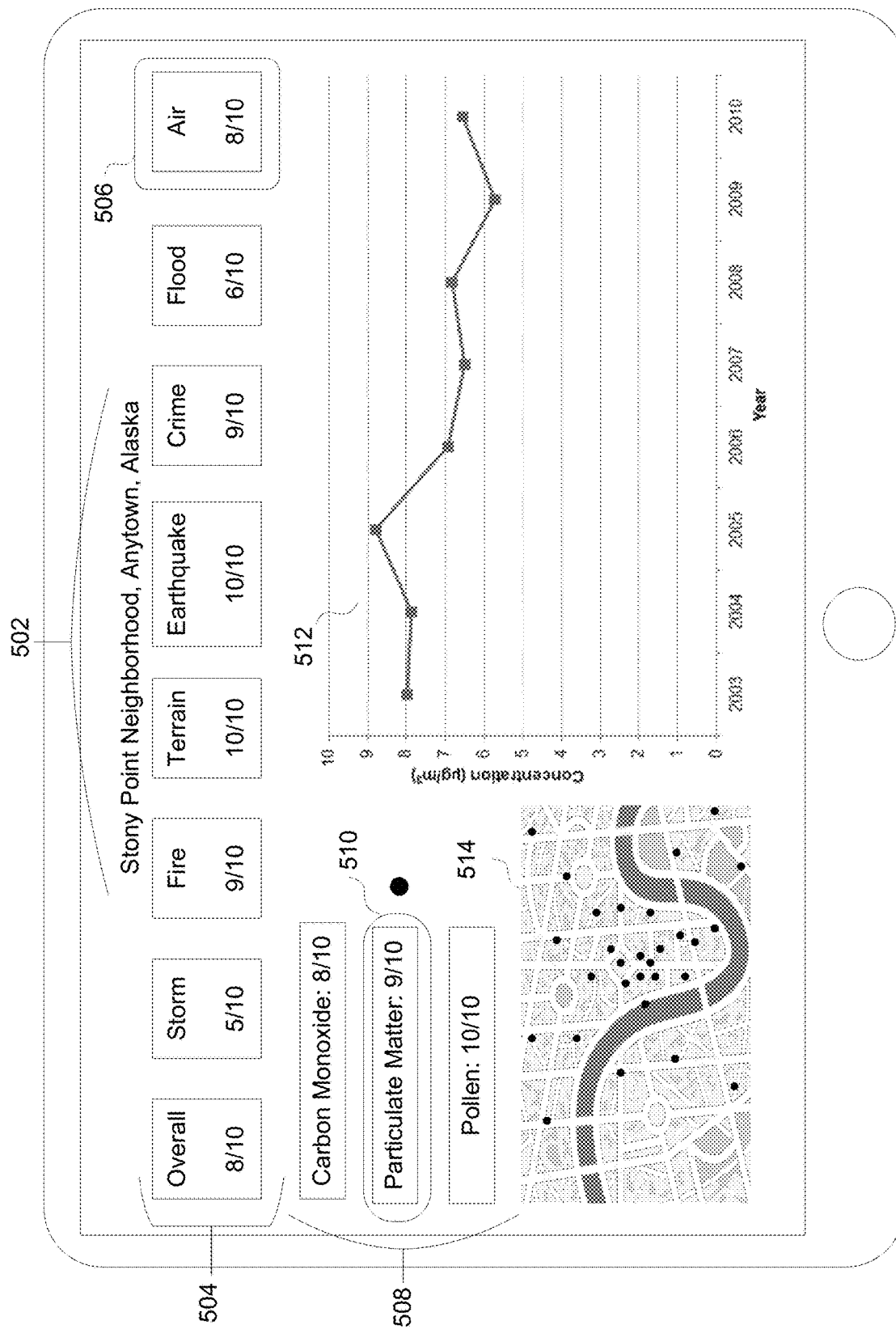
FIG. 5 illustrates an example of a user interface display that may be used in one or more aspects of the disclosure.

FIG. 5 illustrates an example of a user interface display that may be used in one or more aspects of the disclosure. The user interface display may be of an application 226 that facilitates one or more methods described herein, e.g., for performing neighborhood safety assessment. The application 226 may be hosted, managed, or otherwise associated with the neighborhood safety system 202, e.g., via applications interface 212. The user interface of the application 226 may display the results of a neighborhood safety assessment for a desired area, as requested by the user. As shown in FIG. 5, the desired area 502 is "Stony Point Neighborhood, Anytown, Ak." The safety assessment may pertain to the desired area. Various safety parameters 504 were used in the safety assessment. Each safety parameter may have an individual safety assessment. As shown, the safety parameters used were "Storms," "Fire," "Terrain," "Earthquake," "Crime," "Flood," and "Air." Furthermore, based on user preferences, the user request sent to the neighborhood safety system 202, and/or system preferences, an overall safety parameter may also be used in the neighborhood safety assessment (e.g., "Overall"). A score may summarize the individual assessment for each of the safety parameters (e.g., Overall: 8/10, Storm: 5/10, Fire: 9/10, etc.). The overall safety parameter and its assessment may be a summary of, sum total of, aggregation of, and/or a holistic analysis of other safety parameters.

A user may select to view the neighborhood safety assessment of at least one safety parameter in further detail. As shown in FIG. 5, a user may select to view the safety assessment for the safety parameter of "Air" (e.g., as in marker 506). The safety assessment may include characteristics and/or values for the respective safety parameter. As shown in FIG. 5, the safety parameter for "Air" may include values for the categories of Carbon Monoxide, Particulate Matter and Pollen, e.g., as shown in marker 508. The values may be in a metric relevant for the characteristic (e.g., micrograms per meters cubed), a percentage, a ratio, etc. A percentage or ratio may be based on favorability or optimal levels, e.g., with 10/10 being the most favorable or optimal. For example, as shown in marker 508, carbon monoxide levels have a favorability of 8/10, particulate matter have a favorability of 9/10, and pollen has a favorability of 10/10. A user may select one or more characteristics for further analysis. For example, a map of the desired area 514 may be displayed, and the map may be overlaid with an indicator of the selected characteristic. As shown, may indicate concentration of the particulate matter, as indicated by block dots. Furthermore, graphs, charts, and/or other diagrams may be displayed to provide further visuals for understanding the selected characteristic. For example, graph 512 depicts the concentration of particulate matter over the years 2003 through 2010. The application may allow the user to select the times and/or duration (e.g., years, months, days, etc.) for viewing the characteristic and/or its values. Furthermore, the application may allow the user to forecast or predict future values of a characteristic of the safety parameter and/or future characteristics of the safety parameter.

The systems, apparatuses, computer-readable media and methods described above may further provide for increased accuracy in identifying risk associated with a home, user, etc. Accordingly, one or more insurance rates, premiums, and the like, may be adjusted based on this more accurate risk.

While the aspects described herein have been discussed with respect to specific examples including various modes of carrying out aspects of the disclosure, those skilled in the art will appreciate that there are numerous variations and permutations of the above described systems and techniques that fall within the spirit and scope of the invention. For example, one of ordinary skill in the art will appreciate that the steps illustrated in the illustrative figures may be performed in other than the recited order, and that one or more steps illustrated may be optional in accordance with aspects of the disclosure. Further, one of ordinary skill in the art will appreciate that various aspects described with respect to a particular figure may be combined with one or more other aspects, in various combinations, without departing from the invention.

What is claimed is:

1. A method comprising:
   receiving, by a computing device having one or more processors and from a user device, a request for generating a neighborhood safety assessment, wherein the request is based on at least an environmental parameter and a social parameter;
   determining, by the computing device and based on global positioning system (GPS) data of the user device, a desired geographic area for the neighborhood safety assessment, the desired geographic area comprising a vicinity defined within a radius span of the user device based on the GPS data;
   determining, by the computing device, the radius span of the vicinity as being associated with and defining a neighborhood, the neighborhood identified based on the GPS data of the user device;
   determining, by the computing device, one or more environmental sensors associated with the desired geographic area;
   causing, by the computing device in real time, one or more environmental sensors to generate a present value for the environmental parameter;
   receiving, by the computing device and from a second device associated with the desired geographic area, an insurance report based on the neighborhood as defined by the radius span and identified based on the GPS data of the user device;
   processing, via one or more natural language processors of the computing device, one or more terms of the insurance report to identify a value of the social parameter;
   generating, by the computing device executing logic via a safety parameter assessment engine comprising a machine learning algorithm trained to generate the neighborhood safety assessment based on the present value for the environmental parameter and based on the value of the social parameter, the neighborhood safety assessment for the desired geographic area; and
   training the machine learning algorithm to generate the neighborhood safety assessment based on at least past environmental data, wherein training comprises:
   acquiring a training data set, including at least past environmental data from a database associated with the one or more environmental sensors, for the machine learning algorithm to be trained;
   generating with the training data, feature vectors, wherein each feature vector includes (1) the past environmental data received within a predetermined period of time, and (2) the temporal and geographical information for each of the received past environmental data; and
   associating each of the feature vectors with current environmental data;
   generate one or more feature weights corresponding to an effect of the past environmental data on the current environmental data at a given location and a given time;
   training the machine learning algorithm using the associated feature vectors and the one or more feature weights;
   store results of the machine learning algorithm, including the one or more feature weights;
   wherein the neighborhood safety assessment comprises:
      a first score for neighborhood safety based on the social parameter,
      a second score for neighborhood safety based on the environmental parameter,
      a third score for neighborhood safety based on a holistic assessment of the social parameter and the environmental parameter, and
      a visual spatial representation of the social parameter and the environmental parameter, the visual spatial representation comprising a display on a user interface of (i) a map of the desired geographic area, (ii) an indicator of at least one of the social parameter and the environmental parameter overlaid on the map, wherein the indicator is associated with a selection of the at least one of the social parameter and the environmental parameter, and (iii) the first score, the second score, and the third score of the neighborhood safety assessment.

2. The method of claim 1, further comprising:
   receiving, by the computing device and via an electronic storage medium, a past value for the environmental parameter; and
   comparing the received past value to the present value of the environmental parameter,
   wherein the generating the neighborhood safety assessment for the desired geographic area is further based on the comparison of the received past value to the present value.

3. The method of claim 2, further comprising:
   generating, based on the comparison of the past value to the present value of the environmental parameter, a catastrophe model for the desired geographic area, wherein the generating the neighborhood safety assessment is further based on the catastrophe model.

4. The method of claim 1,
wherein the request is further based on one or both of a second environmental parameter or a second social parameter;
wherein the neighborhood safety assessment further comprises:
a fourth score for neighborhood safety based on the one or both of the second environmental parameter or the second social parameter, and
a visual spatial representation of the one or both of the second social parameter and the second environmental parameter; and
wherein the third score for neighborhood safety is further based on a holistic assessment of the social parameter, the environmental parameter, and the one or both of the second environmental parameter or the second social parameter.

5. The method of claim 1, further comprising:
receiving, by the computing device and from a third device associated with the desired geographic area, a criminal activity report associated with the desired geographic area and indicating a second value of the social parameter; and
wherein the generating the neighborhood safety assessment for the desired geographic area is further based on the second value of the social parameter.

6. The method of claim 1, further comprising:
receiving a value of a property in the desired geographic area; and
determining a quantitative effect of the generated neighborhood safety assessment, based on the present value for the environmental parameter and the value of the social parameter, on the value of the property in the desired geographic area.

7. The method of claim 1, further comprising:
updating, based on the generated neighborhood safety assessment based on the present value for the environmental parameter and the value of the social parameter, an insurance policy associated with the insurance report.

8. The method of claim 1, wherein the environmental parameter comprises at least one of:
a pollutant level;
a pollen level;
a precipitation level;
a temperature;
an indication of humidity;
a wind speed or velocity;
an indication of a weather event;
a seismograph reading;
a characteristic of a terrain; and
an indication of a microbe or disease presence.

9. The method of claim 1, wherein the social parameter comprises at least one of:
a frequency of, a severity of, or a count of a crime or misdemeanor; a frequency, severity, or a count of a civil unrest;
a frequency, severity, or a count of a cybercrime; and
a count of residents or workers in the desired geographical area with a criminal record.

10. The system of method of claim 1, wherein the machine learning algorithm comprises a neural network model trained to generate the neighborhood safety assessment.

11. A method comprising:
receiving, by a computing device having one or more processors and from a user device, a request for generating a neighborhood safety assessment, wherein the request is based on at least an environmental parameter and a social parameter;
determining, by the computing device and based on global positioning system (GPS) data of the user device, a desired geographic area for the neighborhood safety assessment, the desired geographic area comprising a vicinity defined within a radius span of the user device based on the GPS data;
determining, by the computing device, the radius span of the vicinity as being associated with and defining a neighborhood, the neighborhood identified based on the GPS data of the user device;
determining, by the computing device, one or more environmental sensors associated with the desired geographic area;
causing, by the computing device in real time, one or more environmental sensors to generate a present value for the environmental parameter;
receiving, by the computing device, one or more electronic files associated with the desired geographic area based on the neighborhood as defined by the radius span and identified based on the GPS data of the user device and describing the environmental parameter and the social parameter;
processing, via one or more natural language processors of the computing device, one or more terms of the one or more electronic files to identify a value of the environmental parameter and a value of the social parameter;
generating, by the computing device executing logic via a safety parameter assessment engine comprising a machine learning algorithm trained to generate the neighborhood safety assessment based on the value of the environmental parameter and the value of the social parameter, the neighborhood safety assessment for the desired geographic area; and
training the machine learning algorithm to generate the neighborhood safety assessment based on at least past environmental data, wherein training comprises:
acquiring a training data set, including at least past environmental data from a database associated with the one or more environmental sensors, for the machine learning algorithm to be trained;
generating with the training data, feature vectors, wherein each feature vector includes (1) the past environmental data received within a predetermined period of time, and (2) the temporal and geographical information for each of the received past environmental data; and
associating each of the feature vectors with current environmental data;
generate one or more feature weights corresponding to an effect of the past environmental data on the current environmental data at a given location and a given time;
training the machine learning algorithm using the associated feature vectors and the one or more feature weights;
store results of the machine learning algorithm, including the one or more feature weights;
wherein the neighborhood safety assessment comprises:
a first score for neighborhood safety based on the social parameter, a second score for neighborhood safety based on the environmental parameter, a third score for neighborhood safety based on a holistic assessment of the social parameter and the environmental parameter, and a visual spatial representation of the social parameter and the environmental parameter, the visual spatial representation comprising a display on a user interface of (i) a map of the desired geographic area, (ii) an indicator of at least one of the social parameter and the environmental parameter overlaid on the map, wherein the indicator is associated with a selection of the at least one of the social parameter and the environmental parameter, and (iii) the first score, the second score, and the third score of the neighborhood safety assessment.

12. The method of claim 11, wherein the request is further based on one or both of a second environmental parameter or a second social parameter;

wherein the neighborhood safety assessment further comprises:

a fourth score for neighborhood safety based on the one or both of the second environmental parameter or the second social parameter, and a visual spatial representation of the one or both of the second social parameter and the second environmental parameter; and wherein the third score for neighborhood safety is further based on a holistic assessment of the social parameter, the environmental parameter, and the one or both of the second environmental parameter or the second social parameter.

13. The method of claim 12, wherein the one or more electronic files comprises at least one of:

a criminal activity report associated with the desired geographic area; or an insurance claim associated with the desired geographic area.

14. The method of claim 11, further comprising:

updating, based on the present value of the environmental parameter, the neighborhood safety assessment of the desired geographic area.

15. A system comprising:

one or more processors;

a natural language processor;

memory storing computer-executable instructions that, when executed by the one or more processors, cause the system to:

receive, from a user device, a request for generating a neighborhood safety assessment, wherein the request is based on at least an environmental parameter and a social parameter;

determine, based on global positioning system (GPS) data of the user device, a desired geographic area for the neighborhood safety assessment, the desired geographic area comprising a vicinity defined within a radius span of the user device based on the GPS data;

determine the radius span of the vicinity as being associated with and defining a neighborhood, the neighborhood identified based on the GPS data of the user device;

identify one or more environmental sensors associated with the desired geographic area;

cause, in real time, the one or more environmental sensors to receive a present value for the environmental parameter;

receive, from a second device associated with the desired geographic area, an insurance report based on the desired geographic area comprising the vicinity defined within the radius span of the user device based on the GPS data;

process, via the natural language processor, one or more terms of the insurance report to identify a value of the social parameter;

generate, by the one or more processors executing logic via a safety parameter assessment engine comprising a machine learning algorithm trained to generate the neighborhood safety assessment based on the present value for the environmental parameter and based on the value of the social parameter, the neighborhood safety assessment for the desired geographic area; and train the machine learning algorithm to generate the neighborhood safety assessment based on at least past environmental data, wherein training comprises:

acquiring a training data set, including at least past environmental data from a database associated with the one or more environmental sensors, for the machine learning algorithm to be trained;

generating with the training data, feature vectors, wherein each feature vector includes (1) the past environmental data received within a predetermined period of time, and (2) the temporal and geographical information for each of the received past environmental data; and associating each of the feature vectors with current environmental data;

generate one or more feature weights corresponding to an effect of the past environmental data on the current environmental data at a given location and a given time;

training the machine learning algorithm using the associated feature vectors and the one or more feature weights;

store results of the machine learning algorithm, including the one or more feature weights;

wherein the neighborhood safety assessment comprises:

a first score for neighborhood safety based on the social parameter, a second score for neighborhood safety based on the environmental parameter, a third score for neighborhood safety based on a holistic assessment of the social parameter and the environmental parameter, and a visual spatial representation of the social parameter and the environmental parameter, the visual spatial representation comprising a display on a user interface of (i) a map of the desired geographic area, (ii) an indicator of at least one of the social parameter and the environmental parameter overlaid on the map, wherein the indicator is associated with a selection of the at least one of the social parameter and the environmental parameter, and (iii) the first score, the second score, and the third score of the neighborhood safety assessment.

16. The system of claim 15, wherein the memory stores additional computer-executable instructions, which when executed by the one or more processors, cause the system to:

receive a past value for the environmental parameter; and compare the past value to the present value for the environmental parameter, wherein the generating the neighborhood safety assessment is further based on the comparison of the past value to the present value.

17. The system of claim 15, wherein the visual spatial representation comprises a plurality of interactive and selectable characteristic markers, wherein selection of one of the plurality of interactive and selectable characteristic markers modifies the visual spatial representation to provide further detail regarding a characteristic associated with the one of the plurality of interactive and selectable characteristic marks.

* * * * *